United States Patent
Lee et al.

(10) Patent No.: US 11,084,879 B2
(45) Date of Patent: Aug. 10, 2021

(54) COMPOSITIONS AND METHODS FOR TREATING PANCREATITIS AND PAIN WITH DEATH RECEPTOR AGONISTS

(71) Applicant: The Johns Hopkins University, Baltimore, MD (US)

(72) Inventors: Seulki Lee, Elkridge, MD (US); Martin G. Pomper, Baltimore, MD (US); Ogyi Park, Elkridge, MD (US); Magdalena Scully, Mount Airy, MD (US); Pankaj J. Pasricha, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 97 days.

(21) Appl. No.: 16/092,142

(22) PCT Filed: Apr. 7, 2017

(86) PCT No.: PCT/US2017/026617
§ 371 (c)(1),
(2) Date: Oct. 8, 2018

(87) PCT Pub. No.: WO2017/177148
PCT Pub. Date: Oct. 12, 2017

(65) Prior Publication Data
US 2019/0119394 A1    Apr. 25, 2019

Related U.S. Application Data

(60) Provisional application No. 62/319,454, filed on Apr. 7, 2016.

(51) Int. Cl.
*A61K 39/395* (2006.01)
*A61K 38/19* (2006.01)
(Continued)

(52) U.S. Cl.
CPC ........ *C07K 16/2878* (2013.01); *A61K 9/0019* (2013.01); *A61K 38/177* (2013.01);
(Continued)

(58) Field of Classification Search
None
See application file for complete search history.

(56) References Cited

U.S. PATENT DOCUMENTS

| 4,816,397 A | 3/1989 | Boss |
| 4,816,567 A | 3/1989 | Cabilly |

(Continued)

FOREIGN PATENT DOCUMENTS

| GB | 2188638 | 10/1987 |
| GB | 2209757 | 5/1989 |

(Continued)

OTHER PUBLICATIONS

Tisato et al., Clinical perspectives of TRAIL: insights into central nervous system disorders, Cell. Mol. Life Sci. 73:2017-2027, Feb. 24, 2016.*

(Continued)

*Primary Examiner* — Claire Kaufman
(74) *Attorney, Agent, or Firm* — Pabst Patent Group LLP

(57) ABSTRACT

Death receptor 5 (DR5) agonist compositions and methods for treating pancreatitis have been developed. The compositions include Tumor Necrosis Factor-related apoptosis-inducing ligand (TRAIL), its analogues, and anti-DR5 agonistic antibodies. In certain embodiments, TRAIL analogs and anti-death receptor 5 agonistic antibodies have analgesic and disease modifying effects on the pancreas.

18 Claims, 18 Drawing Sheets

Specification includes a Sequence Listing.

(51) Int. Cl.
    *C07K 16/28* (2006.01)
    *A61K 47/60* (2017.01)
    *A61K 38/17* (2006.01)
    *A61P 1/18* (2006.01)
    *A61K 9/00* (2006.01)

(52) U.S. Cl.
    CPC ............... *A61K 47/60* (2017.08); *A61P 1/18* (2018.01); *A61K 38/19* (2013.01); *C07K 2317/21* (2013.01); *C07K 2317/73* (2013.01); *C07K 2317/75* (2013.01)

(56) References Cited

U.S. PATENT DOCUMENTS

| | | | |
|---|---|---|---|
| 5,565,332 A | 10/1996 | Hoogenboom | |
| 5,624,821 A | 4/1997 | Winter | |
| 5,721,367 A | 2/1998 | Kay | |
| 5,763,223 A | 6/1998 | Wiley | |
| 5,837,243 A | 11/1998 | Deo | |
| 5,939,598 A | 8/1999 | Kucherlapati | |
| 6,072,047 A | 6/2000 | Rauch | |
| 6,130,364 A | 10/2000 | Jakobovits | |
| 6,180,377 B1 | 1/2001 | Morgan et al. | |
| 6,194,551 B1 | 2/2001 | Idusogie et al. | |
| 6,329,148 B1 | 12/2001 | Rosen | |
| 6,331,415 B1 | 12/2001 | Cabilly | |
| 6,908,963 B2 | 6/2005 | Roberts | |
| 7,060,272 B2 | 6/2006 | Ni | |
| 7,160,924 B2 | 1/2007 | Kinstler | |
| 7,186,699 B2 | 3/2007 | Harding | |
| 7,368,295 B2 | 5/2008 | Tovar | |
| 7,521,056 B2 | 4/2009 | Chang | |
| 7,534,866 B2 | 5/2009 | Chang | |
| 7,550,143 B2 | 6/2009 | Chang | |
| 7,615,233 B2 | 11/2009 | Yano | |
| 7,795,404 B1 | 9/2010 | Lin | |
| 7,897,730 B2 * | 3/2011 | Yu ........................ | A61P 35/00 530/387.1 |
| 7,906,118 B2 | 3/2011 | Chang | |
| 7,994,281 B2 | 8/2011 | Tur | |
| 8,003,111 B2 | 8/2011 | Chang | |
| 8,008,261 B2 | 8/2011 | Badley | |
| 8,029,783 B2 | 10/2011 | Adams | |
| 8,034,352 B2 | 10/2011 | Chang | |
| 8,075,916 B2 | 12/2011 | Song | |
| 8,143,380 B2 | 3/2012 | Walker | |
| 8,158,129 B2 | 4/2012 | Chang | |
| 8,198,033 B2 | 6/2012 | Austin | |
| 8,282,934 B2 | 10/2012 | Chang | |
| 8,287,888 B2 | 10/2012 | Song | |
| 8,435,540 B2 | 5/2013 | Chang | |
| 8,440,787 B2 | 5/2013 | McManus | |
| 8,461,311 B2 | 6/2013 | Hawkins | |
| 8,568,721 B2 | 10/2013 | Radin | |
| 8,586,020 B2 | 11/2013 | Song | |
| 8,597,659 B2 | 12/2013 | Chang | |
| 8,628,801 B2 | 1/2014 | Garreta | |
| 8,673,923 B2 | 3/2014 | El-Deiry | |
| 8,709,409 B2 | 4/2014 | Okuda | |
| 8,986,684 B2 | 3/2015 | Wang | |
| 9,017,726 B2 | 4/2015 | Song | |
| 9,102,735 B2 | 8/2015 | Govindan | |
| 9,150,846 B2 | 10/2015 | Jefferies | |
| 9,901,620 B2 * | 2/2018 | Lee ................... | C07K 14/70578 |
| 2002/0058029 A1 | 5/2002 | Hanna | |
| 2002/0061525 A1 | 5/2002 | Yelin | |
| 2002/0169123 A1 | 11/2002 | El-Deiry | |
| 2004/0005314 A1 | 1/2004 | Escandon | |
| 2004/0146896 A1 | 7/2004 | Rong | |
| 2004/0146968 A1 | 7/2004 | Chung | |
| 2004/0186051 A1 | 9/2004 | Kelley | |
| 2005/0203142 A1 | 9/2005 | Zeldis | |
| 2006/0141561 A1 | 6/2006 | Kelley | |
| 2006/0188498 A1 | 8/2006 | Ashkenazi | |
| 2006/0228352 A1 | 10/2006 | Schoenberger | |
| 2007/0066800 A1 | 3/2007 | Sidhu | |
| 2008/0044421 A1 | 2/2008 | Ashkenazi | |
| 2008/0199423 A1 | 8/2008 | Godowski | |
| 2008/0305038 A1 | 12/2008 | Rosenecker | |
| 2009/0022683 A1 | 1/2009 | Song | |
| 2009/0081157 A1 | 3/2009 | Kornbluth | |
| 2009/0203599 A1 | 8/2009 | Lee | |
| 2009/0203671 A1 | 8/2009 | Glaser | |
| 2009/0258017 A1 | 10/2009 | Callahan | |
| 2009/0324616 A1 | 12/2009 | Stassi | |
| 2009/0325867 A1 | 12/2009 | Cohen | |
| 2010/0068302 A1 | 3/2010 | Ramirez De Molina | |
| 2010/0105620 A1 | 4/2010 | Bowdish | |
| 2010/0209490 A1 | 8/2010 | Morita | |
| 2010/0239554 A1 | 9/2010 | Schellenberger | |
| 2011/0020273 A1 | 1/2011 | Chang | |
| 2011/0038855 A1 | 2/2011 | Schoenberger | |
| 2011/0104103 A1 | 5/2011 | Heetebrij | |
| 2011/0165265 A1 | 7/2011 | Samali | |
| 2011/0200552 A1 | 8/2011 | Rodrigues Dos Reis | |
| 2011/0262455 A1 | 10/2011 | Samali | |
| 2012/0021995 A1 | 1/2012 | Bowdish | |
| 2013/0079280 A1 | 3/2013 | Baca | |
| 2013/0101553 A1 | 4/2013 | Kisseleva | |
| 2013/0150566 A1 | 6/2013 | Hua | |
| 2013/0178416 A1 | 7/2013 | Chilkoti | |
| 2013/0195884 A1 | 8/2013 | Boutros | |
| 2013/0217091 A1 | 8/2013 | Chang | |
| 2014/0004081 A1 | 1/2014 | Cobbold | |
| 2014/0004120 A1 | 1/2014 | Ohtsuka | |
| 2014/0079722 A1 | 3/2014 | Prudent | |
| 2014/0086907 A1 | 3/2014 | Shah | |
| 2014/0096274 A1 | 4/2014 | Quax | |
| 2014/0105898 A1 | 4/2014 | Thomas | |
| 2014/0134647 A1 | 5/2014 | Benedict | |
| 2014/0135377 A1 | 5/2014 | Westermarck | |
| 2014/0161766 A1 | 6/2014 | Chang | |
| 2014/0178398 A1 | 6/2014 | Ashkenazi | |
| 2014/0206843 A1 | 7/2014 | Zhou | |
| 2015/0038511 A1 | 2/2015 | Schafer | |
| 2015/0056159 A1 | 2/2015 | Kontermann | |
| 2015/0056204 A1 | 2/2015 | Holland | |
| 2015/0174269 A1 | 6/2015 | Govindan | |
| 2015/0183875 A1 | 7/2015 | Cobbold | |
| 2015/0197730 A1 | 7/2015 | Shah | |
| 2015/0204877 A1 | 7/2015 | Westermarck | |
| 2015/0218282 A1 | 8/2015 | Shah | |
| 2015/0250896 A1 | 9/2015 | Zhao | |
| 2015/0259397 A1 | 9/2015 | Lee | |
| 2015/0284416 A1 | 10/2015 | Zhao | |
| 2015/0301058 A1 | 10/2015 | Schettini | |
| 2016/0022776 A1 | 1/2016 | Lee | |

FOREIGN PATENT DOCUMENTS

| | | |
|---|---|---|
| KR | 1020020010363 | 2/2002 |
| WO | 98031383 | 7/1998 |
| WO | 9900423 | 1/1999 |
| WO | 99058572 | 11/1999 |
| WO | 2000069911 | 11/2000 |
| WO | 0122987 | 4/2001 |
| WO | 2004001009 | 12/2003 |
| WO | 2004022004 | 3/2004 |
| WO | 2006028939 | 3/2006 |
| WO | 2006042848 | 4/2006 |
| WO | 2006107617 | 10/2006 |
| WO | 2006107786 | 10/2006 |
| WO | 2007046893 | 4/2007 |
| WO | 2007075534 | 7/2007 |
| WO | 2007102690 | 9/2007 |
| WO | 2007145457 | 12/2007 |
| WO | 2008120832 | 10/2008 |
| WO | 2008130066 | 10/2008 |
| WO | 2009058379 | 5/2009 |
| WO | 2009126558 | 10/2009 |
| WO | 2009140469 | 11/2009 |
| WO | 2010093395 | 8/2010 |
| WO | 2010121559 | 10/2010 |
| WO | 2011025904 | 3/2011 |

(56) References Cited

FOREIGN PATENT DOCUMENTS

| WO | 11079293 | 6/2011 | | |
|---|---|---|---|---|
| WO | 2011106707 | 9/2011 | | |
| WO | 2014044768 | 3/2014 | | |
| WO | 2014126537 | 8/2014 | | |
| WO | WO-2014121093 A1 * | 8/2014 | ......... | C07K 14/4703 |
| WO | 2015010615 | 1/2015 | | |
| WO | 2015028850 | 3/2015 | | |
| WO | 2015037000 | 3/2015 | | |
| WO | 15092756 | 6/2015 | | |
| WO | 2015127685 | 9/2015 | | |
| WO | 2015164217 | 10/2015 | | |

OTHER PUBLICATIONS

Ischikawa et al., TRAIL-R2 (DR5) mediates apoptosis of synovial fibroblasts in rheumatoid arthritis, J. Immunol. 171:1061-69, 2003.*

Tisato et al., Intranasal administration of recombinant TRAIL down-regulates CXCL-1/KC in an ovalbumin-induced airway inflammation murine model, PLoS One, 9(12):e115387 ; doi:10.1371/journal.pone.01115387, 2014.*

Mews et al., Pancreatic stellate cells respond to inflammatory cytokines: potential role in chronic pancreatitis, Gut, 50:535-541, 2002.*

Bachem et al. (Chapter 38: Fibrogenesis of the pancreas: the role of stellate cells, in The Pancreas: An Integrated Textbook of Basic Science, Medicine, and Surgery, Second Edition Edited by Begeretal., Blackwell Publishing Limited, pp. 383-392, 2008.*

Johns Hopkins Medicine, FAQs about Chronic Pancreatitis, [Retrieved online Sep. 18, 20] <URL:]https://www.hopkinsmedicine.org/gastroenterology_hepatology/diseases_conditions/faqs/chronic_pancreatitis.html>. 2020.*

Zheng et al., Rolel of immune cells and immune-based therapies in pancreatitis and pancreatic ductal adenocarinoma, Gastroenterol. 144:1230-1240, 2013.*

Lemke et al., Getting TRAIL back on track for cancer therapy, Cell Death Diff. 21:1350-1364, 2014.*

Han et al., Pancreatic stellate cells contribute pancreatic cancer pain via activation of sHH signaling pathway, Oncotarget, 7(14): 18146-18158, Feb. 27, 2016.*

Meng et al., Parenteral analgesics for pain relief in acute pancreatitis: A systematic review, Pancreatology, 13:201-206, 2013.*

Hirsova et al., Death receptor-mediated cell death and proinflammatory signaling in nonalcoholic steatohepatitis, Cell. Mol. Gastroenterol. Hepatol. (1):17-27, 2015.*

Akram, et al., "Alveolar epithelial cells in idiopathic pulmonary fibrosis display upregulation of Trail, DR4 and DR5 expression with simultaneous preferential over-expression of pro-apoptotic marker p53", Int. J. Clin. Exp. Pathol., 7(2):552-564 (2014).

Al-Sabah, et al., "A model for receptor-peptide binding at the glucagon-like peptide-1(GLP-1) receptor through the analysis of truncated ligands and receptors", Br J Pharma, 140:339-46 (2003).

Alconcel, et al., "FDA-approved poly(ethylene glycol)-protein conjugate drugs", Polymer Chemistry, 2(7):1442-48 (2011).

Amiram, et al., "Injectable protease-operated depots of glucagon-like peptide-1 provide extended and tunable glucose control", PNAS, 110(8):2792-7 (2013).

Anel, et al., "Apo2L/TRAIL and immune regulation", Front Biosci., 12:2074-84 (2007).

Angal, et al., "A single amino acid substitution abolishes the heterogeneity of chimeric mouse/human (IgG4) antibody", Mol. Immunol. 30:105-8 (1993).

Apte, et al., "Battle-scarred pancreas: role of alcohol and pancreatic stellate cells in pancreatic fibrosis", J Gastroenterol Hepatol,. 21 Suppl 3:S97-S101 (2006).

Ashkenazi, et al., "Ligand-based targeting of apoptosis in cancer: the potential of recombinant human apoptosis ligand 2/Tumor necrosis factor-related apoptosis-inducing ligand (rhApo2L/TRAIL)", J Clin Oncol, 26(21):3621-30 (2008).

Audo, et al., "The two directions of TNF-related apoptosis-inducing ligand in rheumatoid arthritis", Cytokine, 63(2):81-90 (2013).

Bajaj, et al., "Conatumumab: a novel monoclonal antibody against death receptor 5 for the treatment of advanced malignancies in adults", Expert Opinion on Biological Therapy, 11(11):1519-1524 (2011).

Bataller, et al., "Hepatic stellate cells as target for treatment of liver fibrosis", Semin Liver Dis, 21(03):437-52 (2001).

Bataller, et al., "Liver fibrosis", Clin. Invest., 115(2):209-18 (2005).

Beljaars, et al., "Albumin modified with mannose 6-phosphate: A potential carrier for selective delivery of antifibrotic drugs to rat and human hepatic stellate cells", Hepatology, 29:1486-93 (1999).

Beljaars, et al., "Successful targeting to rat hepatic stellate cells using albumin modified with cyclic peptides that recognize the collagen type VI receptor", J Biol Chem., 275:12743-51 (2000).

Benedict, et al., "TRAIL: not just for tumors anymore", J. Exp. Med., 209(11):1903-6 (2012).

Bertola, et al., "Mouse model of chronic and binge ethanol feeding (the NIAAA model)", Nat Protoc, 8(3):627-37 (2013).

Bhattacharyya, et al., "Understanding fibrosis in systemic sclerosis: shifting paradigms, emerging opportunities", Nat Rev Rheumatol, 8(1):42-54 (2012).

Boerner, et al., "Production of antigen-specific human monoclonal antibodies from in vitro-primed human splenocytes", J. Immunol., 147(1):86-95 (1991).

Brocchini, et al., "PEGylation of native disulfide bonds in proteins", Nature protocols, 1:2241-52 (2006).

Byeon, et al., "Human serum albumin-TRAIL conjugate for the treatment of rheumatoid arthritis", Bioconjug Chem., 25(12):2212-21 (2014).

Chae, et al., "Improved antitumor activity and tumor targeting of NH(2)-terminal-specific PEGylated tumor necrosis factor-related apoptosis-inducing ligand.", Molecular cancer therapeutics 9(6):1719-29 (2010).

Cong, et al., "Site-specific PEGylation at histidine tags". Bioconjugate Chemistry, 23(2):248-63 (2012).

Cuello, et al., "Synergistic induction of apoptosis by the combination of trail and chemotherapy in chemoresistant ovarian cancer cells", Gynecol Oncol., 81(3):380-90 (2001).

De Clerck, "B lymphocytes and humoral immune responses in rheumatoid arthritis", Clinical Rheumatol., 14 Suppl 2:14-8 (1995).

Definition of Dimer, Thefreedictionary.com, 2 pages, accessed Dec. 8, 2014.

Definition of Trimer, thefreedictionary.com, 2 pages, accessed Dec. 8, 2014.

Deng, et al., "Chronic alcohol consumption accelerates fibrosis in response to cerulein-induced pancreatitis in rats", Am J Pathol,. 166(1):93-106 (2005).

Erkan, et al., "StellaTUM: current consensus and discussion on pancreatic stellate cell research", Gut. 61(2):172-8 (2012).

European Search Report for EP 12804683 dated Nov. 20, 2014.

Fee, et al., "Size comparison between proteins PEGylated with branched and linear poly(ethylene glycol) molecules", Biotechnol Bioeng., 98(4):725-3 (2007).

Friedman, "Evolving challenges in hepatic fibrosis", Nat Rev Gastroenterol Hepatol. 7(8):425-36 (2010).

Friedman, "Fibrogenic cell reversion underlies fibrosis regression in liver", PNAS, 109(24):9230-1 (2012).

Gieffers, "APG350 induces superior clustering of TRAIL receptors and shows therapeutic antitumor efficacy independent of cross-linking via Fcγ receptors", Mol Cancer Ther., 12(12):2735-47 (2013).

Gong, et al., "Site-specific PEGylation of exenatide analogues markedly improved their glucoregulatory activity", Br J Pharmacol., 163(2):399-412 (2011).

Harith, et. al., "On the TRAIL of obesity and diabetes", Trends Endocrinol Matabol, 24(11): 578-587 (2013).

Harris, et al., "Effect of pegylation on pharmaceuticals", Nat Rev Drug Discov, 2(3):214-21 (2003).

Hasel, et al., "In chronic pancreatitis, widespread emergence of TRAIL receptors in epithelia coincides with neoexpression of TRAIL by pancreatic stellate cells of early fibrotic areas", Laboratory Investigation, 83(6):825-836 (2003).

(56) References Cited

OTHER PUBLICATIONS

Herbst, et al., "Phase I dose-escalation study of recombinant human Apo2L/TRAIL, a dual proapoptotic receptor agonist, in patients with advanced cancer", J. Clin. Oncol., 28(17):2839-46 (2010).
Ho, et al., "Fibrosis—a lethal component of systemic sclerosis", Nat Rev Rheumatol , 10(7): 390-402 (2014).
International Search Report and Written Opinion for PCT/US2015/020015 dated Jul. 8, 2015.
International Search Report for corresponding PCT application PCT/US2015/026513 dated Jun. 7, 2015.
International Search Report for PCT/US2016/067145 dated Mar. 27, 2017.
International Search Report for PCT/US2017/026617 dated Jul. 4, 2017.
Iredale, et al., "Mechanisms of spontaneous resolution of rat liver fibrosis. Hepatic stellate cell apoptosis and reduced hepatic expression of metalloproteinase inhibitors", J Clin Invest, 102(3):538-49 (1998).
Jakobovits, et al., "Germ-line transmission and expression of a human-derived yeast artificial chromosome", Nature, 362:255-8 (1993b).
Jeffrey, et al., "1,25-Dihydroxyvitamin D3 and IL-2 combine to inhibit T cell production of inflammatory cytokines and promote development of regulatory T cells expressing CTLA-4 and FoxP3", The Journal of Immunology, 183:5458-5467 (2009).
Jiang, et al., "PEGylated TNF-related apoptosis-inducing ligand (TRAIL) for effective tumor combination therapy", Biomaterials, 32:8529-8537 (2011).
Jin, et al, "Effect of tumor necrosis factor-related apoptosis-inducing ligand on the reduction of joint inflammation in experimental rheumatoid arthritis", J. Pharmacol. Exp. Ther. 332(3):858-65 (2010).
Jo, et al., "Apoptosis induced in normal human hepatocytes by tumor necrosis factor-related apoptosis-inducing ligand", Nature Med., 6(5):564-7 (2000).
Jones, et al., "Replacing the complementarity-determining regions in a human antibody with those from a mouse", Nature, 321:522-5 (1986).
Kelner, "Nota Bene: Innocent Inclusions", Science, 282:643 (1998).
Kelley, et al., "Preclinical Studies to Predict the Disposition of Apo2L/Tumor Necrosis Factor-Related Apoptosis-Inducing Ligand in Humans: Characterization of in Vivo Efficacy, Pharmacokinetics, and Safety", J Pharmacol. Exp. Ther., 299(1):31-8 (2001).
Kim, et al., "A sulfate polysaccharide/TNF-related apoptosis-inducing ligand (TRAIL) complex for the long-term delivery of Trail in poly(lactic-co-glycolic acid) (PLGA) microspheres", J Pharm Pharmacol., 65(1):11-21 (2013).
Kim, et al., "Bioimaging for targeted delivery of hyaluronic Acid derivatives to the livers in cirrhotic mice using quantum dots", ACS Nano, 4(6):3005-14 (2010b).
Kim, et al., "Ionic complex systems based on hyaluronic acid and PEGylated TNF-related apoptosis-inducing ligand for treatment of rheumatoid arthritis", Biomaterials, 31(34):9057-64 (2010a).
Kim, et al., "PEGylated TNF-related apoptosis-inducing ligand (TRAIL) analogues: Pharmacokinetics and antitumor effects", Bioconjugate chemistry, 22(8):1631-7 (2011a).
Kim, et al., "PEGylated TNF-related apoptosis-inducing ligand (TRAIL)-loaded sustained release PLGA microspheres for enhanced stability and antitumor activity", J Control Release, 150(1):63¬-9 (2011b).
Kim, et al., "Preparation and characterization of Apo2L/TNF-related apoptosis-inducing ligand-loaded human serum albumin nanoparticles with improved stability and tumor distribution", J Pharm Sci., 100(2):482-91 (2011c).
Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).
Kim, et al., "The secretable form of trimeric TRAIL, a potent inducer of apoptosis", BBRC, 321:930-5 (2004).
Kinstler, et al, "Mono-N-terminal poly(ethylene glycol)-protein conjugates", Adv Drug Deliv., 54:477-85 (2002).
Lakner, et al., "Inhibitory effects of microRNA 19b in hepatic stellate cell-mediated fibrogenesis", Hepatology, 56(1):300-10 (2012).
Lamhamedi-Cherradi, et al., "Defective thymocyte apoptosis and accelerated autoimmune diseases in TRAIL-/- mice", Nat. Immunol., 4(3):255-60 (2003).
Lee, et al., "1004 Treatment with PEGylated TNF-related apoptosis-inducing ligand (TRAIL) induces apoptosis of human rheumatoid arthritis (RA) fibroblast-like synoviocytes (FLS) and suppresses arthritis in murine collagen-induced arthritis", Arthritis and Rheumatism, 72nd Annual scientific meeting of the American college of Rheumatology/43rd annual scientific meeting, Wiley San Francisco, CA, 58(9): Suppl S:s539 (2008).
Lee, et al., "A novel-trail-based therapy for chronic pancreatitis", Gastroenterology, 152(5):XP029979046 (2017). Abstract.
Lemke, et al., "Getting TRAIL back on track for cancer therapy", Cell Death Differ, 21(9):1350-64 (2014).
Li, et al., "Anti-DR5 mAb ameliorate adjuvant arthritis rats through inducing synovial cells apoptosis", Exp biology Med, 234(12):1468-76 (2009).
Liao, et al., "Trail reduced joint inflammation, osteoclast activation and and loss in experimental arthritis", Allergy, 68(98):67 (2013).
Liu, et al., "CII-DC-AdTRAIL cell gene therapy inhibits infiltration of CII-reactive T cells and CII-induced arthritis", J Clin Invest., 112(9):1332-41 (2003).
Louis, et al., "Interleukin-10 controls neutrophilic infiltration, hepatocyte proliferation, and liver fibrosis induced by carbon tetrachloride in mic", Hepatology, 28:1607-15 (1998).
Ma, et al., "Tnf inhibitor therapy for rheumatoid arthritis (Review)", Biomed Reports, 1(2):177-84 (2012).
Mackay and Ambrose, "The TNF family members BAFF and APRIL: the growing complexity", Cytokine Growth Factor Rev, 14(3-4):311-24 (2003).
Mackay and Kalled, "TNF ligands and receptors in autoimmunity: an update", Curr Opin Immunol, 14: 783-90 (2002).
Marks, et al., "By-passing immunization. Human antibodies from V-gene libraries displayed on phage", J. Mol. Biol., 222:581-97 (1991).
Martinez-Lostao, et al., "Liposome-bound APO2L/TRAIL is an effective treatment in a rabbit model of rheumatoid arthritis", Arthritis Rheum., 62(8):2272-82 (2010).
Mayo Clinic, "Diabetes", www.mayoclinic.org/diseases-conditions/diabetes/in-depth/diabetes-symthoms/art, 2 pages, accessed Dec. 19, 2014.
McInnes, et al., "Cytokines in the pathogenesis of rheumatoid arthritis", Nature Rev Immunol., 7(6):429-42 (2007).
Miranda-Carus, et al., "Rheumatoid arthritis synovial fluid fibroblasts express TRAIL-R2 (DR5) that is functionally active", Arthritis Rheum., 50(9):2786-93 (2004).
Molineux, "The design and development of pegfilgrastim (PEG-rmetHuG-CSF, Neulasta)", Curr Pharm Des., 10(11):1235-44 (2004).
Nikpour, et al., "Mortality in systemic sclerosis: lessons learned from population-based and observational cohort studies", Curr Opin Rheumatol, 26(2):131-7 (2014).
Omary, et al., "The pancreatic stellate cell: a star on the rise in pancreatic diseases", J Clin Invest, 117(1):50-59 (2007).
Park, et al., "Down-regulation of Fox0-dependent c-FLIP expression mediates Trail-induced apoptosis in activated hepatic stellate cells", Cell Signal., 21(10):1495-503 (2009).
Pavet, et al., "Multivalent DR5 peptides activate the TRAIL death pathway and exert tumoricidal activity", Cancer Res., 70:1101-10, (2010).
Pinzani, "Pancreatic stellate cells: new kids become mature", Gut, 55(1):12-14 (2006).
Poelstra, et al., "Drug targeting to the diseased liver", J. Control Release, 161(2):188-97 (2012).
Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).
Reichling and Levine, "Critical role of nociceptor plasticity in chronic pain", Trends Neurosci, 32(12):611-8 (2009).

(56) References Cited

OTHER PUBLICATIONS

Riechmann, et al., "Reshaping human antibodies for therapy", Nature, 332:323-7 (1988).
Rieux-Laucat, et al, "Cell-death signaling and human disease", Curr Opin Immunol, 15:325-31 (2003).
Shibata, et al., "Functionalization of tumor necrosis factor-a using phase display technique and PEGylation improves its antitumor therapeutic window", Clin Cancer Res., 10:8293-300 (2004).
Song, et al., "Tumor necrosis factor-related apoptosis-inducing ligand (TRAIL) is an inhibitor of autoimmune inflammation and cell cycle progression", J Exp Med., 191(7):1095-104 (2000).
Strejan, et al, "Suppression of chronic-relapsing experimental allergic encephalomyelitis in strain-13 guinea pigs by administration of liposome-associated myelin basic protein", J. Neuroimmunol, 7(1):27-41 (1984).
Taimr, "Activated stellate cells express the TRAIL receptor-2/death receptor-5 and undergo TRAIL-mediated apoptosis", Hepatology, 37(1):89-95 (2003).
TNFSF10, symbol report, http://www.genenames.org/data/hgnc_data.php?hgnc_id=11925, 1 page, downloaded Mar. 8, 2011.
Tur, et al., "DR4-selective tumor necrosis factor-related apoptosis-inducing ligand (TRAIL) variants obtained by structure-based design", J. Biological Chemistry, 283(29):20560-8 (2008).
Van Der Sloot, "Designed tumor necrosis factor-related apoptosis-inducing ligand variants initiating apoptosis exclusively via the DR5 receptor", PNAS,103(23):8634-9 (2006).
Varga, et al., "Systemic sclerosis: a prototypic multisystem fibrotic disorder", J. Clin Invest, 117(3):557-67 (2007).
Verhoeyen, et al., "Reshaping human antibodies: grafting an antilysozyme activity", Science, 239:1534-6 (1988).
Wahl, "Increased apoptosis induction in hepatocellular carcinoma by a novel tumor-targeted TRAIL fusion protein combined with bortezomib", Hepatology, 57(2):625-36 (2013).
Walczak, et al., "Tumoricidal activity of tumor necrosis factor-related apoptosis-inducing ligand in vivo", Nature Med., 5(2):157-63 (1999).
Wang, et al., "Small-molecule activation of the TRAIL receptor DR5 in human cancer cells", Nature Chemical Biology, 9:84-9 (2013).
Wu, et al., "Regression of human mammary adenocarcinoma by systemic administration of a recombinant gene encoding the hFlex-TRAIL fusion protein", Mole Therapy, 3(3):368-74 (2001).
Wu, et al., "TRAIL and chemotherapeutic drugs in cancer therapy", Vitam Horm., 67:365-83 (2004).
Xiang, et al., "Tissue distribution, stability, and pharmacokinetics of APO2 ligand/tumor necrosis factor-related apoptosis-inducing ligand in human colon carcinoma COLO205 tumor-bearing nude mice", Drug Metab Dispo., 32(11):1230-8 (2004).
Yamamoto, et al., "Site-specific PEGylation of a lysine-deficient TNF-a with full bioactivity", Nature BioTech., 21:545-52 (2003).
Yang, et al., "Target specific hyaluronic acid-interferon alpha conjugate for the treatment of hepatitis C virus infection", Biomaterials 32(33);8722-9 (2011).
Yao, et al., "Intra-articular adenoviral-mediated gene transfer of trail induces apoptosis of arthritic rabbit synovium", Gene therapy, 10(12):1055-60 (2003).
Yoshioka, et al., "Optimal site-specific PEGylation of mutant TNF-alpha improves its antitumor potency", Biochem Biophys Res Comm., 315:808-14 (2004).
Youn, et al., "Biological and physicochrmical evaluation of the conformational stability of tumor nrcrosis factor-related apoptosis-inducing ligand (TRAIL)", Biotechnol Lttrs., 29:713-21 (2007).
Youn, et al., "PEGylated apoptotic protein-loaded PLGA microspheres for cancer therapy", International Journal of Nanomedicine, 2015:739 (2015).
Zemel, et al. "Dietary calcium and dairy products modulate oxidative and inflammatory stress in mice and humans", Journal of Nutrition, 138:1047-1052 (2008).
Zhu, et al., "A Novel Therapeutic Approach Targeting TRAIL signaling reveals a role for activated pancreatic stellate cells in the pathogenesis of pain in chronic pancreatitis", Gastroenterology, 150(4):5916-5917 (2016).
Zhu, et al., "Transforming growth factor beta induces sensory neuronal hyperexcitability, and contributes to pancreatic pain and hyperalgesia in rats with chronic pancreatitis", Mol Pain, 8:65 (2012).
Klonowski-Stumpe, et al., "Apoptosis in activated rat panreatic stellate cells", Am. J. Physiol. Gastrointest. Liver Physiol., 283:819-826 (2002).
Pan, et al., "site-specific PEGylation of a mutated-cysteine residue and its effect on tumor necrosis factor (TNF)-related apoptosis0inducing ligand (TRAIL)", Biomaterials, 34(36): 9115-9123 (2013).
Hironobu, "Updated Diagnosis/severity criteria of intractable systemic autoimmune disease, Systemic scleroderma", *Inflammation & Immunity*, 23(6):517-521 (Oct. 2015) with English Summary.
Darby, et al., "Fibroblasts and myofibroblasts in wound healing", Clin. Cosmetic Invest. Dermatol., 47:301-311 (2014).
Fox, et al., "Tumor necrosis factor-related apoptosis-inducing ligand (TRAIL) receptor-1 and receptor-2 agonists for cancer therapy", Exp. Opin Biol. Ther., 10:1-18 (2010).
Golan-Gerstl, et al., "Epithelial cell apoptosis by Fas ligand-positive myofibroblats in lung fibrosis", Am. J. Respir. Cel. Mol. Biol., 36:270-275 (2007).
Kendall, et al., "p75 neurotrophin receptor signaling regulates hepatic myofibroblasts proliferation and apoptosis in recovery from rodent liver fibrosis", Hepatol., 49:901-910 (2009).
Ley, et al., "How Mouse macrophages sense what is going on, [Retrieved online: URL:https://doi.org/10.3389/fimmu.2016.00204., on Apr. 24, 2020] Frontiers Immunol., 7" 204 (1-17) (2016).
Lorusso, et al., "First-in-human study of AMG 655, a pro-apoptotic TRAIL receptor-2 agonist, in adult patients with advanced solid tumors", J. Clin. Oncol. ASCO Meeting Abstracts, 25(18 Suppl):3534, (2007).
Saleh, et al., "A phase I study of CS-1008 (humanized monoclonal antibody targeting death receptor 5 or DR5), administered weekly to patients with advanced solid tumors or lymphomas", J. Clin. Oncol., 26(15 Suppl.):3537 (2008).
Shih, et al., Inhibition of a novel fibrogenic factor TIIa reverses established colonic fibrosisNature, 7(6):1492-1503 (2014).
Tarrats, et al., "Critical role of tumor necrosis factor receptor 1, but not 2, in hepatic stellate cell proliferation, extracellular matrix remodeling, and liver fibrogenesis", Hepatol., 54:319-327 (2011).
Wegner, et al., "Edar is a downstream target of beta-catenin and drives collagen accumulation in the mouse prostrate", Biology Open, bio037945. doi:10.1242/bio.037945, 8:1-6 (2019).
Yurovsky, et al., "Cross-talk between TRAIL and TGF-beta in regulation of collagen production in scleroderma lung disease", Arthritis Res. Ther., 6:26 (2004).
Yurovsky, et al., "Effect of TRAIL on collagen produciton by human lung fibroblasts", FASEB J., 15(5):A1045 (2001).
Bhanot, et al., "Dichotomy of fates of pancreatic epithelia in chronic pancreatitis: apoptosis versus survival", Trends in Molecular Medicine, 12(8):351-357 (2006).
Dumnicka, et al., "Osteoprotegerin, trail and osteoprotegerin/trail ratio in patients at early phase of acute pancreatitis.", Folia Medica Cracoviensia, 54(2):17-26 (2014), Abstract only.
Li, et al., "The role of TRAIL signal pathway in acute pancreatitis", Hepato-Gastroenterology, 60(124):912-915 (2013).

* cited by examiner

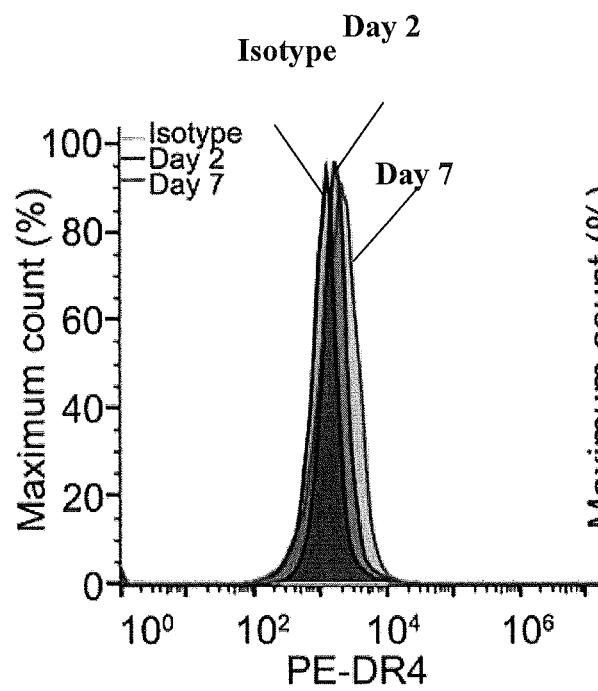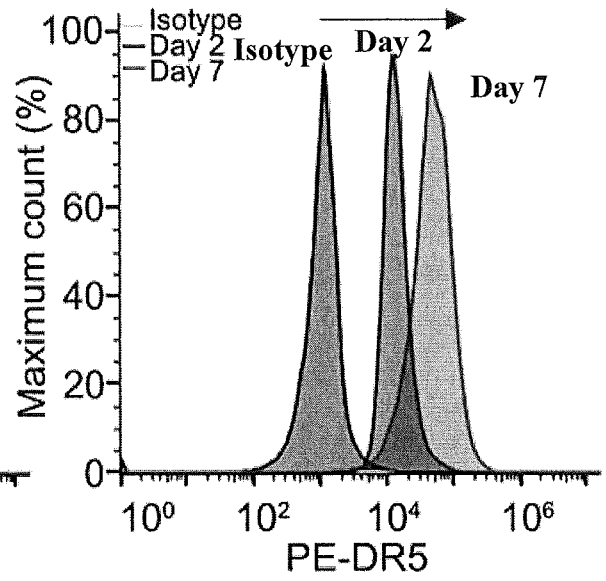
FIG 6A                              FIG. 6B

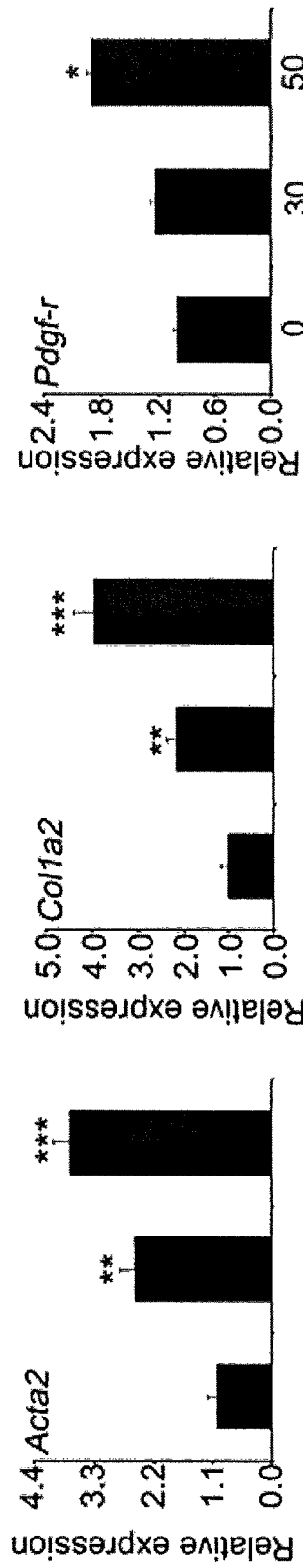
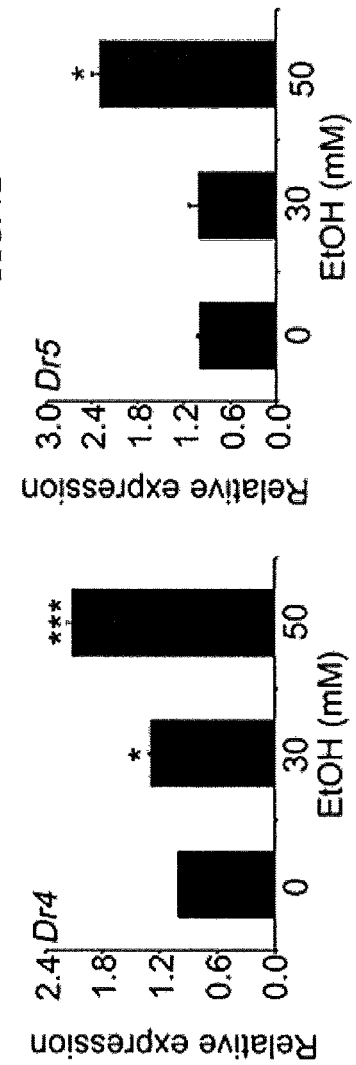
FIG. 7A  FIG. 7B  FIG. 7C  FIG. 7D  FIG. 7E

COMPOSITIONS AND METHODS FOR TREATING PANCREATITIS AND PAIN WITH DEATH RECEPTOR AGONISTS

CROSS-REFERENCE TO RELATED APPLICATIONS

This application is a National Phase application under 35 U.S.C. 371 of PCT/US2017/026617, filed Apr. 7, 2017, which claims benefit of and priority to U.S. Provisional Application No. 62/319,454, filed Apr. 7, 2016, which are hereby incorporated herein by reference in their entirety.

STATEMENT REGARDING FEDERALLY SPONSORED RESEARCH OR DEVELOPMENT

This invention was made with government support under AA023855 awarded by the National Institutes of Health and W81XWH-15-1-0301 and W81XWH-15-1-0302 awarded by the Army Medical Research and Materiel Command. The government has certain rights in the invention.

REFERENCE TO SEQUENCE LISTING

The Sequence Listing submitted Apr. 3, 2017, as a text file named "JHU_C_13835_PCT_ST25.txt," created on Apr. 3, 2017, and having a size of 4,380 bytes is hereby incorporated by reference.

BACKGROUND OF THE INVENTION

The tumor necrosis factor receptor superfamily (TNFRSF) is a group of cytokine receptors characterized by the ability to bind tumor necrosis factors (TNFs) via an extracellular cysteine-rich domain. With the exception of nerve growth factor (NGF), all TNFs are homologous to the archetypal TNF-alpha. In their active form, the majority of TNF receptors form trimeric complexes in the plasma membrane. Accordingly, most TNF receptors contain transmembrane domains (TMDs), although some can be cleaved into soluble forms (e.g. TNFR1), and some lack a TMD entirely (e.g. DcR3). In addition, most TNF receptors require specific adaptor protein such as TRADD, TRAF, RIP and FADD for downstream signaling. TNF receptors are primarily involved in apoptosis and inflammation, but they can also take part in other signal transduction pathways, such as proliferation, survival, and differentiation. TNF receptors are expressed in a wide variety of tissues in mammals, especially in leukocytes.

The term death receptor refers to those members of the TNF receptor superfamily that contain a death domain, such as TNFR1, Fas receptor, DR4 and DR5. They were named for their role in apoptosis (programmed cell death), although they are now known to have other functions.

The term TNF receptor is often used to refer to the archetypal members of the superfamily, namely TNFR1 and TNFR2, which recognize TNF-alpha. There are 27 family members including: Tumor necrosis factor receptor 1, Tumor necrosis factor receptor 2, Lymphotoxin beta receptor, OX40, CD40, Fas receptor, Decoy receptor 3, CD27, CD30, 4-1BB, Death receptor 4 (DR4), Death receptor 5 (DR5), Decoy receptor 1, Decoy receptor 2, RANK, Osteoprotegerin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor.

Pancreatitis, acute or chronic, is a significant contributor to the "burden of gastrointestinal disease" in the United States, according to several surveys. Chronic pancreatitis (CP) is a serious consequence of alcohol abuse and is characterized by progressive and irreversible destruction of pancreas structure and function. CP is accompanied by pancreatic fibrosis and constant abdominal pain. Pain in CP has been very difficult to treat. The lack of understanding about the underlying biology has led to various empirical approaches that are often based on purely anatomical grounds, and generally highly invasive.

Therefore, there is a substantial unmet need for therapeutic strategies that treat pancreatitis.

It is an object of the invention to provide compositions for treating pancreatitis, pancreatic fibrosis, and pancreatic pain.

It is another object of the invention to provide methods for treating pancreatitis, pancreatic fibrosis, and pancreatic pain.

SUMMARY OF THE INVENTION

A method of treating pancreatitis and associated disorders such as pain with death receptor agonists, for example, recombinant human TRAIL analogs or anti-death receptor 5 (DR5) agonistic antibodies, have been developed. Recombinant TNF (Tumor Necrosis Factor)-related apoptosis-inducing ligand (TRAIL) analogs and anti-DR5 antibodies selectively target activated pancreatic stellate cells and reduce inflammation, fibrogenesis, and pain and improve pancreatic functions in acute and chronic pancreatitis in individuals in need thereof.

Methods of treating pancreatitis or pancreatic pain and improving pancreatic functions include administering to a subject suffering from or at risk of suffering from pancreatitis, pancreatic fibrosis or disorder, e.g. pancreatic pain, a pharmaceutical composition containing an effective amount of a death receptor agonist Suitable death receptor agonists include, but are not limited to, TRAIL-R2 (death receptor 5) agonists such as recombinant human (rh) TRAIL, rhTRAIL analogs, engineered TRAIL analogs, long-acting TRAIL proteins modified, for example, with polymers such as poly(ethylene glycol), copolymers and branched analogs, and biopolymers such as hyaluronic acid. TRAIL-based long-acting formulations including TRAIL fusion proteins, agonistic anti-TRAIL-R2 antibodies, and agonistic small molecules or peptide molecules binding TRAIL-R2. TRAIL-R2 (DR5), but not DR4, is a major receptor inducing selective apoptosis in activated pancreatic stellate cells, as demonstrated in Example 3.

In preferred embodiments, the TRAIL is rhTRAIL (i.e., recombinant human TRAIL), or a functional fragment or variant thereof, for example, a fragment of a 281 amino acid human TRAIL. In preferred embodiments, the fragment has an amino acid sequence from 114 to 281 or from 95 to 281 of the full-length 281 amino acid human form. In preferred embodiments, long-acting rhTRAIL is a PEGylated Tumor necrosis factor (TNF)-related apoptosis inducing ligand (TRAIL) protein, a PEGylated TRAIL derivative, or any combination thereof. In preferred embodiments, anti-death receptor antibodies are anti-death receptor 5 agonistic antibodies. In an exemplary aspect, the death receptor agonists contain a PEGylated TRAIL analog and anti-DR5 agonistic antibodies.

Also provided herein are death receptor agonists and one or more polyethylene glycol (PEG) moieties or derivatives thereof. In some cases, the death receptor agonist includes a PEGylated TRAIL analog or derivative thereof.

In one aspect, the PEG moiety or derivative is selected from the group consisting of linear PEG, branched PEG, Star PEG, Comb PEG, dendrimeric PEG, PEG succinimidylpropionate, PEG N-hydroxysuccinimide, PEG propionaldehyde, PEG maleimide, linear methoxypoly(ethylene glycol) (mPEG), branched mPEG, Star mPEG, Comb mPEG, dendrimeric mPEG, mPEG succinimidylpropionate, mPEG N-hydroxysuccinimide, mPEG propionaldehyde, and mPEG maleimide. In some cases, the branched PEG moiety or derivative includes monomeric, dimeric and/or trimeric PEG moieties, or derivatives thereof. In some cases, the PEG moiety or derivative is trimeric methoxypolyethylene glycol maleimide.

The PEG moiety has a molecular weight of at least 1,000 daltons As measured by size-exclusion chromatography or MALDI-TOF mass spectra. In some cases, the PEG moiety includes a PEG moiety with an average molecular weight between about 1,000 and 1,000,000 daltons, an average molecular weight between about 10,000 and 500,000 daltons, an average molecular weight between about 1,000 and 100,000 daltons, most preferably between 5,000 and 50,000 daltons. In other cases, the PEG moiety includes a PEG moiety with an average molecular weight between about 20,000 and 250,000 daltons, an average molecular weight between about 30,000 and 100,000 daltons, or a PEG moiety with an average molecular weight between about 40,000 and 80,000 daltons.

Also provided are compositions containing anti-DR5 is conatumumab, tigatuzumab, lexatumuman, HGS-TR2J/KMTR-2, LBY135, drozitumab, TAS266, DS-8273/DS-8273a, APG880, or RG7386.

Exemplary diseases or disorders include acute or chronic pancreatitis, pancreatitis-related pain and pancreatic fibrosis as well as fibrosis-related pain. In some cases, pancreatic fibrosis includes desmoplasia at a tumor microenvironment in the pancreas. In an exemplary embodiment, the fibrotic disorder is fibrosis-related pain. In some cases, the methods further include identifying a patient suffering from or at risk of developing fibrosis-related pain.

Suitable modes of administration include by injection, including intravenous and subcutaneous, inhalation, pulmonary, nasal, and possibly intraocular. The compositions may be administered at a dose of 0.001 mg/kg to 100 mg/kg, e.g., 0.001 mg/kg, 0.01 mg/kg, 0.1 mg/kg, 0.5 mg/kg, 1.0 mg/kg, 2.0 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg. Preferably, the compositions are administered at a dose of between 0.2 mg/kg and 20 mg/kg, or a dose between 0.001 mg/kg and 20 mg/kg. The formulations are administered in a dosage and period of time effective so that pancreatic tissues are protected, fibrotic formation is reduced, pancreatic fibrogenesis is reversed, pain is reduced, and healthy pancreatic tissues are unharmed. In one aspect, treating a fibrotic disease or disorder includes reducing inflammation.

BRIEF DESCRIPTION OF THE DRAWINGS

FIGS. 6A and 6B are graphs showing expression profiles of DR4 or DR5 on cell membrane of quiescent PSCs (Day 2) and activated PSCs (Day 7), measured by flow cytometry suing PE-tagged death receptor antibodies. DR5 predominantly expressed on cellular surface of activated PSCs compared to DR4.

FIGS. 7A-7E are bar graphs showing that ethanol (EtOH)-activated primary human PSCs upregulate Acta2 (α-SMA, activated stellate cells marker), fibrogenic markers and TRAIL receptors (DR5/DR4). FIGS. 7A-7E depict qPCR analysis of PSCs activated by EtOH (30 and 50 mM). *$P<0.05$, $P<0.01$, *$P<0.001$ vs. non-EtOH activated PSCs.

FIG. 10A is a diagram of representative tracings showing increased spontaneous and induced action potentials in neurons cultured with PSC-CM. This is accompanied by a significant decrease in rheobase (the amount of current needed to elicit an action potential) (see FIG. 10B). FIG. 10C shows enhanced evoked action potentials. FIG. 10D shows increased action potential amplitude. FIG. 10E shows decreased IA currents (transient Kv currents important for maintaining excitability).

DETAILED DESCRIPTION OF THE INVENTION

I. Definitions

Figure 1:
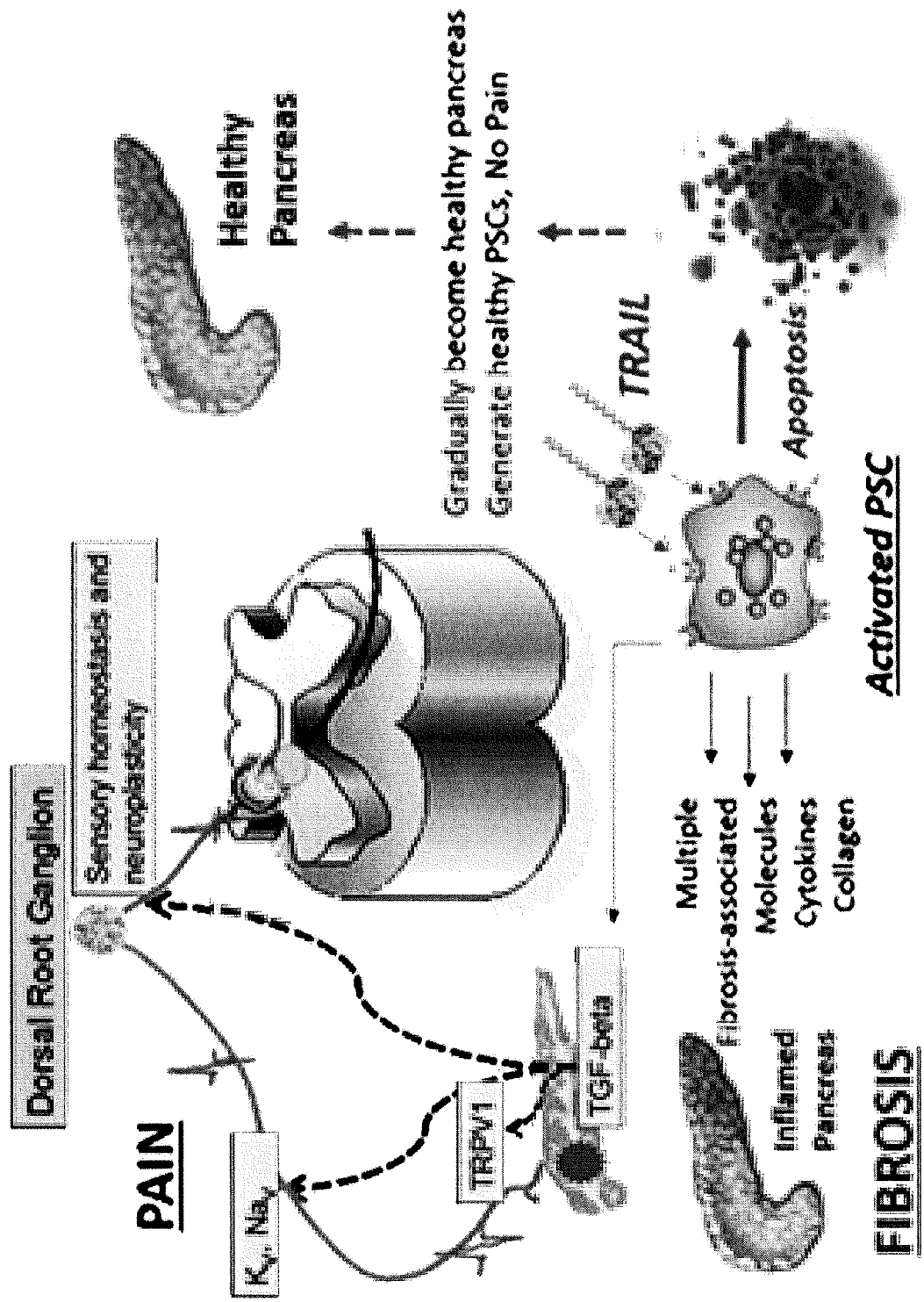
FIG. 1 is a schematic showing the role of death receptor (DR) agonists, e.g. TRAIL analogs or anti-DR agonistic antibodies, in the pancreatitis models. Death receptor agonists selectively targets activated pancreatic stellate cells (PSCs) in the pancreas while leaving other tissues unharmed. Activated PSCs are one of the originators of pancreatic fibrosis and pain. By selectively blocking PSC activation and/or eradicating activated PSCs, death receptor agonists reduce fibrosis and pain leading to repair of pancreatic tissue.

By "ameliorate" is meant decrease, suppress, attenuate, diminish, arrest, or stabilize the development or progression of a disease.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence or amount of the analyte to be detected.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate one or more of the symptoms of a disease or disorder relative to an untreated patient. The effective amount of for therapeutic treatment of a disease varies depending upon the manner of administration, the age, body weight, and general health of the subject. Ultimately, the attending physician or veterinarian will decide the appropriate amount and dosage regimen.

By "modulate" is meant alter (increase or decrease). Such alterations are detected by standard art known methods such as those described herein.

"Fibrotic disease or disorder" is a general term for the progressive formation of excess fibrous connective tissue in an organ or tissue in a reparative or reactive process. Fibrosis can occur in many tissues of the body, typically as a result of inflammation or damage. Examples of organs or tissues susceptible to fibrosis include but are not limited to: lungs, pancreas, heart, liver, skin, fingers, joints, brain, bone marrow, penis, and intestine The term, "normal amount" refers to a normal amount of a complex in an individual known not to be diagnosed with a disease or disorder. The amount of the molecule can be measured in a test sample and compared to the "normal control level," utilizing techniques such as reference limits, discrimination limits, or risk defining thresholds to define cutoff points and abnormal values (e.g., for pancreatitis). The "normal control level" means the level of one or more proteins (or nucleic acids) or combined protein indices (or combined nucleic acid indices) typically found in a subject known not to be suffering from prostate cancer. Such normal control levels and cutoff points may vary based on whether a molecule is used alone or in a formula combining other proteins into an index. Alternatively, the normal control level can be a database of protein patterns from previously tested subjects who did not convert to a disease or disorder over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

The phrase "pharmaceutically acceptable carrier" is art recognized and includes a pharmaceutically acceptable material, composition or vehicle, suitable for administering compounds to individuals in need thereof.

The term "TNF (Tumor Necrosis Factor)-related apoptosis-inducing ligand (TRAIL) receptor agonist" as used herein refers to those agents that bind to and activate death receptors (DRs), TRAIL-R1 (DR4) and TRAIL-R2 (DR5). TRAIL receptor agonists, or TRAs, include, but are not limited to, recombinant TRAIL, recombinant TRAIL variants, TRAIL derivatives and anti-TRAIL receptor antibodies binding to TRAIL-R1 and/or TRAIL-R2 as well as agonistic small molecules or peptide molecules binding TRAIL-R1 and/or TRAIL-R2. In some embodiments, anti-TRAIL receptor antibodies include antibodies to TRAIL-R2 (DR5).

In some embodiments, TRAIL antibodies include, but are not limited to, those DR5 antibodies initially developed for cancer therapy, conatumumab, tigatuzumab, lexatumuman, HGS-TR2J/KMTR-2, LBY135, drozitumab, TAS266, DS-8273/DS-8273a, APG880, RG7386.

The term "PEGylation" refers to a process of covalent or non-covalent attachment or amalgamation of polyethylene glycol (PEG) polymer chains to molecules and macrostructures, such as a drug, therapeutic protein or vesicle.

The terms "prevent", "preventing", "prevention", and "prophylactic treatment" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

Pharmaceutical compositions may be assembled into kits or pharmaceutical systems for use in arresting cell cycle in rapidly dividing cells, e.g., cancer cells. Kits or pharmaceutical systems may include a carrier means, such as a box, carton, or tube, having in close confinement therein one or more container means, such as vials, tubes, ampoules, bottles, syringes, or bags. The kits or pharmaceutical systems of the disclosure may also include associated instructions for using the kit.

II. Compositions

Useful compositions include death receptor (TRAIL receptor) agonists. Examples of death receptor agonists include purified TRAIL, isolated TRAIL, recombinant TRAIL, recombinant TRAIL variants, TRAIL derivatives and anti-TRAIL receptor antibodies binding to TRAIL-R1 and/or TRAIL-R2 as well as agonistic small molecules or peptide molecules binding TRAIL-R1 and/or TRAIL-R2. In some embodiments, anti-TRAIL receptor antibodies include antibodies to TRAIL-R1 (DR4) and TRAIL-R2 (DR5).

A. Death Receptor Agonists

Compositions are for use in methods of treating pancreatitis and fibrotic diseases and disorders of the pancreas with death receptor TRAIL-R1 (DR4) and TRAIL-R2 (DR5) agonists such as PEGylated TNF (Tumor Necrosis Factor)-related apoptosis-inducing ligand (TRAIL) analog and anti-DR5 agonistic antibody, to reduce inflammation, fibrogenesis, and pain and improve pancreatic functions in the pancreas and pancreatitis. These PEGylated protein-based drug and anti-DR5 antibody have disease-modifying effects in pancreatitis and pancreatic fibrosis as well as pain. They are safe, highly stable, and potent, with an extended half-life.

1. Trail

TNF (Tumor Necrosis Factor)-related apoptosis-inducing ligand (TRAIL), is a protein functioning as a ligand that induces the process of cell death called apoptosis. TRAIL is a cytokine that is produced and secreted by most normal tissue cells. It causes apoptosis primarily in tumor cells, by binding to certain death receptors. TRAIL has also been designated CD253 (cluster of differentiation 253) and TNFSF10 (tumor necrosis factor (ligand) superfamily, member 10).

In humans, the gene that encodes TRAIL is located at chromosome 3q26, which is not close to other TNF family members. The genomic structure of the TRAIL gene spans approximately 20 kb and is composed of five exonic segments 222, 138, 42, 106, and 1245 nucleotides and four introns of approximately 8.2, 3.2, 2.3 and 2.3 kb. The TRAIL gene lacks TATA and CAAT boxes and the promotor region contains putative response elements for GATA, AP-1, C/EBP, SP-1, OCT-1, AP3, PEA3, CF-1, and ISRE.

TRAIL shows homology to other members of the tumor necrosis factor superfamily. It is composed of 281 amino acids and has characteristics of a type II transmembrane protein (i.e. no leader sequence and an internal transmembrane domain). The N-terminal cytoplasmic domain is not conserved across family members, however, the C-terminal extracellular domain is conserved and can be proteolytically cleaved from the cell surface. TRAIL forms a homo-trimer that binds three receptor molecules.

TRAIL binds to the death receptors DR4 (TRAIL-R1) and DR5 (TRAIL-R2). The process of apoptosis is caspase-8-dependent. Caspase-8 activates downstream effector caspases including procaspase-3, -6, and -7, leading to activation of specific kinases. TRAIL also binds the receptors DcR1 and DcR2, which do not contain a cytoplasmic domain (DcR1) or contain a truncated death domain (DcR2). DcR1 functions as a TRAIL-neutralizing decoy-receptor. The cytoplasmic domain of DcR2 is functional and activates NFkappaB. In cells expressing DcR2, TRAIL binding therefore activates NFkappaB, leading to transcription of genes known to antagonize the death signaling pathway and/or to promote inflammation. TRAIL has been shown to interact with TNFRSF10B.

TRAIL may be obtained in a native or genetically engineered (recombinant) form. TRAIL may include a zipper amino acid motif favoring trimer formation and/or a terminal group facilitating isolation and purification thereof.

Suitable TRAIL proteins include TRAIL in the human form, which has an amino acid sequence of 281 amino acids in length, SEQ ID NO: 1:

MAMMEVQGGPSLGQTCVLIVIFTVLLQSLCVAVTYVYFTNELKQMQ

DKYSKSGIACFLKEDDSYWDPNDEESMNSPCWQVKWQLRQLVRKM

ILRTSEETISTVQEKQQNISPLVRERGPQRVAAHITGTRGRSNTLSSPN

SKNEKALGRKINSWESSRSGHSFLSNLHLRNGELVIHEKGFYYIYSQT

YFRFQEEIKENTKNDKQMVQYIYKYTSYPDPILLMKSARNSCWSKD

AEYGLYSIYQGGIFELKENDRIFVSVTNEHLIDMDHEASFFGAFLVG.

In preferred embodiments, TRAIL has an amino acid sequence from arginine-114 (Arg, R) to glycine-281 (Gly, G) of the full-length human form (1-281), and has an amino acid sequence of SEQ ID NO: 2:

```
RERGPQRVAAHITGTRGRSNTLSSPNSKNEKALGRKINSWESSRSGHS

FLSNLHLRNGELVIHEKGFYYIYSQTYFRFQEEIKENTKNDKQMVQYI

YKYTSYPDPILLMKSARNSCWSKDAEYGLYSIYQGGIFELKENDRIFV

SVTNEHLIDMDHEASFFGAFLVG.
```

Typically, TRAIL is modified with ethylene glycol (EG) units, more preferably 2 or more EG units (i.e., polyethylene glycol (PEG)) at an N-terminal amino acid residue. The N-terminal amino acid residue includes, but is not limited to, lysine, cysteine, serine, tyrosine, histidine, phenylalanine, or arginine.

Typically, any TRAIL analogue may be suitable for PEGylation. Analogues include trimeric TRAIL wherein at least one of the three monomers has an amino acid sequence of SEQ ID NOS: 1 or 2, with one or more amino acid substitutions or deletions. The TRAIL analogues may be generated in vitro using routine molecular biology techniques.

TRAIL may be attached to a leucine or an isoleucine zipper (ILZ) at its N-terminus. In preferred embodiments, the zipper motif is an isoleucine zipper (Kim et al., *BBRC*, 321:930-935(2004)).

2. Death Receptor Agonistic Antibodies

In some embodiments, death receptor agonistic antibodies include, but are not limited to, DR5 antibodies conatumumab, tigatuzumab, lexatumuman, HGS-TR2J/KMTR-2, LBY135, drozitumab, TAS266, DS-8273/DS-8273a, APG880, RG7386, or chimeric antibodies, with single, dual or multiple antigen or epitope specificities, and fragments, such as F(ab')2 and the like, including hybrid fragments. Such antibodies and fragments can be made by techniques known in the art and can be screened for specificity and activity according to general methods for producing antibodies and screening antibodies for specificity and activity (see, e.g., Harlow and Lane. Antibodies, A Laboratory Manual. Cold Spring Harbor Publications, New York, (1988)).

Many non-human antibodies (e.g., those derived from mice, rats, or rabbits) are naturally antigenic in humans and, thus, can give rise to undesirable immune responses when administered to humans. Therefore, the use of human or humanized antibodies in the methods described herein serves to lessen the chance that an antibody administered to a human will evoke an undesirable immune response. A humanized or chimeric death receptor agonistic antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a death receptor agonistic antibody also includes at least a portion of an immunoglobulin constant region (Fc), typically that of a human immunoglobulin. The constant domains of the death receptor agonistic antibodies may be selected with respect to the proposed function of the antibody, in particular the effector function which may be required. In some embodiments, the constant domains of the death receptor agonistic antibodies are (or include) human IgA, IgD, IgE, IgG or IgM domains.

Antibody fragments include the binding and binding specificity of the antibody (and do not require a particular biological function of the antibody constant regions), such as a binding fragment specific to death receptors. Other antibody regions can be substituted, altered, or both, with or from any heavy and light chains or portions thereof, with the expectation that the bi-specific binding and binding specificity for the target death receptor will be retained. For antibody fragment and peptide forms, the binding fragment specific to death receptor can be embodied by any of numerous binding fragment forms and can be linked in any suitable way, including in any of the multivalent and multi-specific ways used for antibody binding fragments. In the case of the disclosed antibodies, antibody fragments, and polypeptides, such forms will be bi-specific instead of (or in addition to) multivalent. Examples of binding fragment forms include $F(ab')_2$, fragment antigen-binding (Fab), half antibodies, single-chain variable fragments (scFv), VhH domain, V-NAR domain, $V_H$ domain, $V_L$ domain, $F(ab)_3$, bis-scFv, diabody, triabody, tetrabody, and minibody. Any of these forms can be independently used to embody the binding fragment specific to death receptor and then can be combined or joined using any suitable linker or coupling. The binding fragment specific to death receptor can also each be used as a binding fragment portion of a multivalent and/or multi-specific form of antibody fragments. Examples include $F(ab')_2$, $F(ab)_3$, bis-scFv, diabody, triabody, tetrabody, and minibody.

3. Analogues of Death Receptor Agonists

The death receptor agonists may be modified to include an additional moiety, thus forming analogues. The moiety may be a polymeric moiety, a polypeptide, a polysaccharide, a labeled tracer, and so on. The moiety may be non-covalently or covalently attached to the death receptor agonists.

In some embodiments, the moiety is a polyalkylene oxide such as polyethylene gycol (PEG). Polyethylene glycol (PEG) is a polyether compound with many applications from industrial manufacturing to medicine. The structure of PEG is (note the repeated element in parentheses): H—(O-CH2-CH2)n-OH PEG is also known as polyethylene oxide (PEO) or polyoxyethylene (POE), depending on its molecular weight. PEG, PEO, or POE refers to an oligomer or polymer of ethylene oxide. The three names are chemically synonymous, but historically PEG is preferred in the biomedical field, whereas PEO is more prevalent in the field of polymer chemistry. Because different applications require different polymer chain lengths, PEG typically is used with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. Very high purity PEG has recently been shown to be crystalline, allowing determination of a crystal structure by x-ray diffraction. Since purification and separation of pure oligomers is difficult, the price for this type of quality is often 10-1000 fold that of polydisperse PEG.

PEGs are also available with different geometries. Branched PEGs have three to ten PEG chains emanating from a central core group. Star PEGs have 10 to 100 PEG chains emanating from a central core group. Comb PEGs have multiple PEG chains normally grafted onto a polymer backbone. The numbers that are often included in the names of PEGS indicate their average molecular weights (e.g. a PEG with n=9 would have an average molecular weight of approximately 400 daltons, and would be labeled PEG 400. Most PEGs include molecules with a distribution of molecular weights (i.e. they are polydisperse). The size distribution can be characterized statistically by its weight average molecular weight (Mw) and its number average molecular weight (Mn), the ratio of which is called the polydispersity index (Mw/Mn). MW and Mn can be measured by mass spectrometry.

PEGylation is the act of covalently coupling a PEG structure to another larger molecule, for example, a therapeutic protein, which is then referred to as a PEGylated protein. PEGylated interferon alfa-2a or -2b are commonly used injectable treatments for Hepatitis C infection. PEG is soluble in water, methanol, ethanol, acetonitrile, benzene, and dichloromethane, and is insoluble in diethyl ether and hexane. It is coupled to hydrophobic molecules to produce non-ionic surfactants. PEGs contain potential toxic impurities, such as ethylene oxide and 1,4-dioxane. Ethylene Glycol and its ethers are nephrotoxic if applied to damaged skin.

Polyethylene glycol is produced by the interaction of ethylene oxide with water, ethylene glycol, or ethylene glycol oligomers. The reaction is catalyzed by acidic or basic catalysts. Ethylene glycol and its oligomers are preferable as a starting material instead of water, because they allow the creation of polymers with a low polydispersity (narrow molecular weight distribution). Polymer chain length depends on the ratio of reactants.

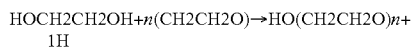

Depending on the catalyst type, the mechanism of polymerization can be cationic or anionic. Polymerization of ethylene oxide is an exothermic process.

PEGylation (also often styled pegylation) is the process of both covalent and non-covalent attachment or amalgamation of polyethylene glycol (PEG) polymer chains to molecules and macrostructures, such as a drug, therapeutic protein or vesicle, which is then described as PEGylated (pegylated). PEGylation is routinely achieved by incubation of a reactive derivative of PEG with the target molecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

PEGylation is the process of attaching the strands of the polymer PEG to molecules, most typically peptides, proteins, and antibody fragments, that can improve the safety and efficiency of many therapeutics. It produces alterations in the physiochemical properties including changes in conformation, electrostatic binding, hydrophobicity etc. These physical and chemical changes increase systemic retention of the therapeutic agent. Also, it can influence the binding affinity of the therapeutic moiety to the cell receptors and can alter the absorption and distribution patterns.

PEG is a particularly attractive polymer for conjugation. The specific characteristics of PEG moieties relevant to pharmaceutical applications are: water solubility, high mobility in solution, lack of toxicity and low immunogenicity, ready clearance from the body, and altered distribution in the body.

The biological activity of a TRAIL derivative can be increased via selective PEGylation. The treatment effect of medications can also be increased through the PEGylation process. Application of PEGylation increases molecular weight, defense of a metabolism site and inhibition of an immunogenicity site, thereby increasing in vivo half-life and stability and reducing immunogenicity. Furthermore, kidney excretion of peptides and proteins bound with PEG is reduced due to the increase of molecular weights of peptides and proteins by PEG, so that PEGylation has advantages of increasing effects in both pharmacokinetically and pharmacodynamically.

Preferably the polyethylene glycol or a derivative thereof is linear or branched, or may be in the form of a dimer or trimer, without or with a linker to the TRAIL and/or the other PEG molecules. Representative polyethylene glycol derivatives include methoxypolyethylene glycol succinimidylpropionate, methoxypolyethylene glycol N-hydroxysuccinimide, methoxypolyethylene glycol propionaldehyde, methoxypolyethylene glycol maleimide, or multiple branched types of these derivatives. Preferably, the polyethylene glycol derivative is linear methoxypolyethylene glycol maleimide, branch type methoxypolyethylene glycol maleimide or trimeric methoxypolyethylene glycol maleimide, and more preferably is trimeric methoxypolyethylene glycol maleimide.

After the TRAIL derivative is PEGylated with polyethylene glycol or the derivative thereof is prepared, the molecular structure of the analogue may be confirmed by a mass spectroscope, a liquid chromatography, an X-ray diffraction analysis, a polarimetry, and comparison between calculated values and measured values of representative elements constituting the PEGylated TRAIL.

4. Excipients

The TRAIL, antibodies, or derivatives may be formulated for administration. Typically for injection, inhalation, pulmonary administration or intraocular administration this will be in the form of a lyophilized or spray dried powder, which can be dissolved for administration with sterile water, buffer, or other excipient such as those listed in Goodman and Gilman's.

The TRAIL derivative PEGylated with polyethylene glycol or a derivative thereof may be prepared as a liquid or suspension, optionally including buffering agents, suspending agents, bacteriostatic agents, or viscosity modified, and then packaged into ampoule or vial unit administration form. The composition is sterilized by filtration, irradiation or a gas such as ethylene oxide.

III. Methods of Making the Compositions

A. Methods of Making TRAIL and PEGylated TRAIL

The first step of the PEGylation is the functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The overall PEGylation processes for protein conjugation can be broadly classified into two types, namely a solution phase batch process and an on-column fed-batch process. The simple and commonly adopted batch process involves the mixing of reagents together in a suitable buffer solution, preferably at a temperature between 4° and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used as a site specific site by conjugation with aldehyde functional polymers. The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc. made available for conjugation.

These heterobifunctional PEGs are very useful in linking two entities, where a hydrophilic, flexible and biocompatible spacer is needed. Preferred end groups for heterobifunctional PEGS are maleimide, vinyl sulfones, pyridyl disulfide, amine, carboxylic acids and NHS esters. Third generation pegylation agents, where the shape of the polymer has been branched, Y shaped or comb shaped are available which show reduced viscosity and lack of organ accumulation. Unpredictability in clearance times for PEGylated compounds may lead to the accumulation of large molecular weight compounds in the liver leading to inclusion bodies with no known toxicologic consequences. Furthermore, alteration in the chain length may lead to unexpected clearance times in vivo.

B. Methods of Making Death Receptor Agonists

The antibodies and antibody fragments can be produced by any method known in the art useful for the production of polypeptides, e.g., in vitro synthesis, recombinant DNA production, and the like. The antibodies may be produced by recombinant DNA technology. The anti-DR5 agonistic antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

The antibodies may also be produced by immunizing animals with synthetic or purified monomeric, homomeric, or heteromeric DR5. The immune sera are applied to a peptide affinity column to generate a highly specific immunoreagent.

The human antibodies and humanized antibodies described herein can be prepared by any known technique. Examples of techniques for human monoclonal antibody production include those described by Boerner et al., J. Immunol., 147(1), 86-95 (1991). Human antibodies described herein (and fragments thereof) can also be produced using phage display libraries (see, e.g., Marks et al., J. Mol. Biol., 222, 581-597 (1991)). The human antibodies described herein can also be obtained from transgenic animals. For example, transgenic mutant mice that are capable of producing a full repertoire of human antibodies in response to immunization have been described (see, e.g., Jakobovits et al., PNAS, 90, 2551-255 (1993); and Jakobovits et al., Nature, 362, 255-258 (1993)).

Methods for humanizing non-human antibodies are known in the art. For example, humanized antibodies can be generated by substituting rodent complementarity-determining regions (CDRs) or CDR sequences for the corresponding sequences of a human antibody. Detailed procedures are disclosed in Jones et al., Nature, 321, 522-525 (1986); Riechmann et al., Nature, 332, 323-327 (1988); Verhoeyen et al., Science, 239, 1534-1536 (1988).

Methods that can be used to produce humanized antibodies are also described in U.S. Pat. Nos. 4,816,567; 5,565,332; 5,721,367; 5,837,243; 5,939,598; 6,130,364; and 6,180,377.

IV. Methods of Use

The death receptor agonists may be used to treat pancreatitis, pancreatic fibrosis, pancreatic pain, or any combination thereof. The death receptor agonists are useful at reducing, stopping, or reversing pancreatic inflammation in the early stages of the inflammatory process, at reducing, stopping, or reversing pancreatic fibrosis, and reducing or stopping pancreatic pain.

The human body dose of the pharmaceutical composition containing the TRAIL derivative PEGylated with polyethylene glycol or a derivative thereof may vary depending on the age, body weight, gender, administration form, health status and level of disease of patients, and may be administrated following decisions of doctors or pharmacists with preferably dose of 0.01 to 200 mg/kg/day.

As described in the exampled, the effect of $TRAIL_{PEG}$ in primary human PSCs was investigated. In particular, the antifibrotic and anti-pain efficacy of intravenously administered $TRAIL_{PEG}$ in different pancreatitis rat models including cerulein-induced acute pancreatitis (AP) and ethanol/cerulein/Lieber-Decarli (LD) diet-induced chronic pancreatitis (CP) was tested. As described herein, TRAIL signaling plays critical roles in pancreatic fibrogenesis as well as TGFβ regulation, which can directly sensitize nociceptors and induce pancreatic hyperalgesia. $TRAIL_{PEG}$ ameliorated the progress of pancreatitis in both acute and chronic phases. Surprisingly, $TRAIL_{PEG}$ treatment significantly reduced pain in CP rat models.

As described in detail below, $TRAIL_{PEG}$ selectively blocks PSC activation and eradicates activated PSCs, an originator of CP, which results in the reversal of CP. Furthermore, by targeting PSCs, which sensitize nociceptors by the upregulation of TGFβ, $TRAIL_{PEG}$ reduces CP-associated severe pain without systemic toxicity.

The role of TRAIL signaling in pancreatic fibrogenesis and pain was examined to determine the feasibility of utilizing a death receptor agonist (e.g., $TRAIL_{PEG}$ and anti-DR5 antibodies) for pancreatitis therapy in the clinic. A new direction in TRAIL signaling towards pancreatitis therapy and novel TRAIL-based regimens is proposed.

A. Conditions to be Treated

Pancreatitis is inflammation of the pancreas. The pancreas is a large organ behind the stomach that produces digestive enzymes. There are two main types, acute pancreatitis and chronic pancreatitis. Signs and symptoms of pancreatitis include pain in the upper abdomen, nausea and vomiting. The pain often goes into the back and is usually severe. In acute pancreatitis a fever may occur and symptoms typically resolve in a few days. In chronic pancreatitis weight loss, fatty stool, and diarrhea may occur. Complications may include infection, bleeding, diabetes mellitus, or problems with other organs.

The most common causes of acute pancreatitis are gallstones and heavy alcohol use. Other causes include direct trauma, certain medications, infections such as mumps, and tumors among others. Chronic pancreatitis may develop as a result of acute pancreatitis. It is most commonly due to many years of heavy alcohol use. Other causes include high levels of blood fats, high blood calcium, some medications, and certain genetic disorders such as cystic fibrosis among others. Smoking increases the risk of both acute and chronic pancreatitis. Diagnosis of acute pancreatitis is based on a threefold increase in the blood of either amylase or lipase. In chronic pancreatitis these tests may be normal. Medical imaging such as ultrasound and CT scan may also be useful.

1. Acute Pancreatitis

Acute pancreatitis is usually treated with intravenous fluids, pain medication, and sometimes antibiotics. Typically, no eating or drinking is allowed and a tube may be placed into the stomach. A procedure known as a endoscopic retrograde cholangiopancreatography (ERCP) may be done to open the pancreatic duct if blocked. In those with gallstones the gallbladder is often also removed. In chronic pancreatitis, in addition to the above, temporary feeding through a nasogastric tube may be used to provide adequate nutrition. Long-term dietary changes and pancreatic enzyme replacement may be required, and, occasionally surgery is done to remove parts of the pancreas.

Acute pancreatitis occurs in about 30 per 100,000 people a year. New cases of chronic pancreatitis develop in about 8 per 100,000 people a year and currently affect about 50 per 100,000 people in the United States. Globally, in 2013 pancreatitis resulted in 123,000 deaths up from 83,000 deaths in 1990. It is more common in men than women. Often chronic pancreatitis starts between the ages of 30 and 40 while it is rare in children. Acute pancreatitis was first described on autopsy in 1882 while chronic pancreatitis was first described in 1946.

The most common symptoms of pancreatitis are severe upper abdominal or left upper quadrant burning pain radiating to the back, nausea, and vomiting that is worse with eating. The physical examination will vary depending on severity and presence of internal bleeding. Blood pressure may be elevated by pain or decreased by dehydration or bleeding. Heart and respiratory rates are often elevated. The abdomen is usually tender but to a lesser degree than the pain itself. As is common in abdominal disease, bowel sounds may be reduced from reflex bowel paralysis. Fever or jaundice may be present. Chronic pancreatitis can lead to diabetes or pancreatic cancer. Unexplained weight loss may occur from a lack of pancreatic enzymes hindering digestion.

Eighty percent of cases of pancreatitis are caused by alcohol or gallstones. Gallstones are the single most common cause of acute pancreatitis. Alcohol is the single most common cause of chronic pancreatitis.

Some medications are commonly associated with pancreatitis, most commonly corticosteroids such as prednisolone, but also including the HIV drugs didanosine and pentamidine, diuretics, the anticonvulsant valproic acid, the chemotherapeutic agents L-asparaginase and azathioprine, estrogen by way of increased blood triglycerides, and antihyperglycemic agents like metformin, vildagliptin, and sitagliptin. The drugs used to treat conditions that are themselves associated with increased events of pancreatitis may also be incidentally linked to pancreatitis. Examples include statins in treatment of dyslipidemia and gliptins in treatment of diabetes. According to the Food and Drug Administration's MedWatch Surveillance System and Published Reports Atypical, atypical antipsychotics such as clozapine, risperidone, and olanzapine can also be responsible for causing pancreatitis.

Other common causes include trauma, mumps, autoimmune disease, high blood calcium, hypothermia, and endoscopic retrograde cholangiopancreatography (ERCP). Pancreas divisum is a common congenital malformation of the pancreas that may underlie some recurrent cases. Diabetes mellitus type 2 is associated with a 2.8-fold higher risk.

Less common causes include pancreatic cancer, pancreatic duct stones, vasculitis (inflammation of the small blood vessels in the pancreas), coxsackie virus infection, and *porphyria*—particularly acute intermittent *porphyria* and erythropoietic protoporphyria.

There is an inherited form that results in the activation of trypsinogen within the pancreas, leading to autodigestion. Involved genes may include Trypsin 1, which codes for trypsinogen, SPINK1, which codes for a trypsin inhibitor, or cystic fibrosis transmembrane conductance regulator.

The common causes of pancreatitis include alcohol/ethanol, gallstones, steroids, trauma autoimmune pancreatitis, mumps, hyperlipidemia, hypothermia, hyperparathyroidism, scorpion sting, endoscopic retrograde cholangiopancreatography, and drugs (typically azathioprine and valproic acid).

A number of infectious agents have been recognized as causes of pancreatitis including: Mumps, Coxsackie virus, Hepatitis B, Cytomegalovirus, Herpes simplex virus, and Varicella-zoster virus.

The differential diagnosis for pancreatitis includes, but is not limited to, Cholecystitis, choledocholithiasis, perforated peptic ulcer, bowel infarction, small bowel obstruction, hepatitis and mesenteric ischemia. Diagnosis requires 2 of the 3 following criteria: characteristic acute onset of epigastric or vague abdominal pain that may radiate to the back (see signs and symptoms above), serum amylase or lipase levels >3 times the upper limit of normal, and an imaging study with characteristic changes. CT, MRI, abdominal ultrasound or endoscopic ultrasound can be used for diagnosis. Amylase and lipase are 2 enzymes produced by the pancreas. Elevations in lipase are generally considered a better indicator for pancreatitis as it has greater specificity and has a longer half-life. For imaging, abdominal ultrasound is convenient, simple, non-invasive, and inexpensive. It is more sensitive and specific for pancreatitis from gall stones than other imaging modalities. However, in 25-35% of patients the view of the pancreas and be obstructed by bowel gas making it difficult to evaluate. A contrast enhanced CT scan is usually performed more than 48 hours after the onset of pain to evaluate for pancreatic necrosis and extra pancreatic fluid as well as predict the severity of the disease. CT scanning earlier can be falsely reassuring. ERCP or an endoscopic ultrasound can also be used if a biliary cause for pancreatitis is suspected.

The treatment of pancreatitis is supportive and depends on severity. Morphine generally is suitable for pain control. There is a claim that morphine may constrict the sphincter of Oddi, but this is controversial. There are no clinical studies to suggest that morphine can aggravate or cause pancreatitis or cholecystitis. The treatment that is received for acute pancreatitis will depend on whether the diagnosis is for the mild form of the condition, which causes no complications, or the severe form, which can cause serious complications. The treatment of mild acute pancreatitis is successfully carried out by admission to a general hospital ward. Traditionally, people were not allowed to eat until the inflammation resolved but more recent evidence suggests early feeding is safe and improves outcomes. Since pancreatitis can cause lung damage and affect normal lung function, oxygen is occasionally delivered through breathing tubes that are connected via the nose. The tubes can then be removed after a few days once it is clear that the condition is improving. Dehydration may result during an episode of acute pancreatitis, so fluids will be provided intravenously. The pain associated with even mild or moderate cases of acute pancreatitis can be severe, which means that a narcotic pain killer may be required.

Severe pancreatitis is associated with organ failure, necrosis, infected necrosis, pseudocyst and abscess. If diagnosed with severe acute pancreatitis, people will need to be admitted to a high dependency unit or intensive care unit. It is likely that the levels of fluids inside the body will have dropped significantly as it diverts bodily fluids and nutrients in an attempt to repair the pancreas. The drop in fluid levels can lead to a reduction in the volume of blood within the body, which is known as hypovolemic shock. Hypovolemic shock can be life-threatening as it can very quickly starve the body of the oxygen-rich blood that it needs to survive. To avoid going into hypovolemic shock, fluids will be pumped intravenously. Oxygen will be supplied through tubes attached to the nose and ventilation equipment may be used to assist with breathing. Feeding tubes may be used to provide nutrients, combined with appropriate analgesia.

As with mild acute pancreatitis, it will be necessary to treat the underlying cause—gallstones, discontinuing medications, cessation of alcohol, etc. If the cause is gallstones, it is likely that an ERCP procedure or removal of the gallbladder will be recommended. The gallbladder should be removed during the same hospital admission or within two weeks of the pancreatitis so as to limit the risk of recurrent pancreatitis. If the cause of pancreatitis is alcohol, cessation of alcohol consumption and treatment for alcohol dependency may improve the pancreatitis. Even if the underlying cause is not related to alcohol consumption, doctors recommend avoiding it for at least six months as this can cause further damage to the pancreas during the recovery process. Oral intake, especially fats, is generally restricted initially but early enteral feeding within 48 hours has been shown to improve clinical outcomes. Fluids and electrolytes are replaced intravenously. Nutritional support is initiated via tube feeding to surpass the portion of the digestive tract most affected by secreted pancreatic enzymes if there is no improvement in the first 72-96 hours of treatment.

Early complications include shock, infection, systemic inflammatory response syndrome, low blood calcium, high blood glucose, and dehydration. Blood loss, dehydration, and fluid leaking into the abdominal cavity (ascites) can lead to kidney failure. Respiratory complications are often severe. Pleural effusion is usually present. Shallow breathing from pain can lead to lung collapse. Pancreatic enzymes may attack the lungs, causing inflammation. Severe inflammation can lead to intra-abdominal hypertension and abdominal compartment syndrome, further impairing renal and respiratory function and potentially requiring management with an open abdomen to relieve the pressure.

Late complications include recurrent pancreatitis and the development of pancreatic pseudocysts—collections of pancreatic secretions that have been walled off by scar tissue. These may cause pain, become infected, rupture and bleed, block the bile duct and cause jaundice, or migrate around the abdomen. Acute necrotizing pancreatitis can lead to a pancreatic abscess, a collection of pus caused by necrosis, liquefaction, and infection. This happens in approximately 3% of cases, or almost 60% of cases involving more than two pseudocysts and gas in the pancreas.

2. Chronic Pancreatitis

Chronic pancreatitis is a long-standing inflammation of the pancreas that alters the organ's normal structure and functions. It can present as episodes of acute inflammation in a previously injured pancreas, or as chronic damage with persistent pain or malabsorption. It is a disease process characterized by irreversible damage to the pancreas as distinct from reversible changes in acute pancreatitis. The annual incidence of chronic pancreatitis is 5 to 12 per 100,000 people, the prevalence is 50 per 100,000. It is more common in men than women.

The symptoms consistent with chronic pancreatitis usually present with persistent abdominal pain or steatorrhea resulting from malabsorption of the fats in food. Significant weight loss often occurs due to malabsorption and can continue to be a health problem as the condition progresses. The patient may also complain about pain related to their food intake, especially those meals containing a high percentage of fats and protein.

Among the causes of chronic pancreatitis are the following: alcohol, autoimmune disorders, intraductal obstruction, idiopathic pancreatitis, tumors, ischemia, and calcific stones. The relationship between etiologic factors, genetic predisposition, and the pace of disease progression requires further clarification, though recent research indicates smoking may be a high-risk factor to develop chronic pancreatitis. In a small group of patients chronic pancreatitis has been shown to be hereditary. Almost all patients with cystic fibrosis have established chronic pancreatitis, usually from birth. Cystic fibrosis gene mutations have also been identified in patients with chronic pancreatitis but in whom there were no other manifestations of cystic fibrosis. Obstruction of the pancreatic duct because of either a benign or malignant process may result in chronic pancreatitis.

The mechanism of chronic pancreatitis viewed from a genetic standpoint indicates early onset of severe epigastric pain beginning in childhood. It is an autosomal dominant disease, chronic pancreatitis disease is identified in the cationic trypsinogen gene PRSS1, and mutation, R122H. R122H is the most common mutation for hereditary chronic pancreatitis with replacement of arginine with histidine at amino acid position 122 of the trypsinogen protein. There are, of course, other mechanisms—alcohol, malnutrition, and smoking—each exhibiting its own effect on the pancreas.

The diagnosis of chronic pancreatitis is based on tests on pancreatic structure and function. Serum amylase and lipase may be moderately elevated in cases of chronic pancreatitis, amylase and lipase are nearly always found elevated in the acute condition. A secretin stimulation test is considered the best test for diagnosis of chronic pancreatitis. Other tests used to determine chronic pancreatitis are serum trypsinogen, computed tomography, ultrasound and biopsy. When chronic pancreatitis is caused by genetic factors, elevations in ESR, IgG4, rheumatoid factor, ANA and anti-smooth muscle antibody may be detected.

The different treatment options for management of chronic pancreatitis are medical measures, therapeutic endoscopy and surgery. Treatment is directed, when possible, to the underlying cause, and to relieve pain and malabsorption. Insulin dependent diabetes mellitus may occur and need long term insulin therapy. The abdominal pain can be very severe and require high doses of analgesics, sometimes including opiates. Alcohol cessation and dietary modifications (low-fat diet) are important to manage pain and slow the calcific process. Antioxidants may help but it is unclear if the benefits are meaningful. Pancreatic enzyme replacement is often effective in treating the malabsorption and steatorrhea associated with chronic pancreatitis. Treatment of CP consists of administration of a solution of pancreatic enzymes with meals. Some patients do have pain reduction with enzyme replacement and since they are relatively safe, giving enzyme replacement to a chronic pancreatitis patient is an acceptable step in treatment for most patients. Treatment may be more likely to be successful in those without involvement of large ducts and those with idiopathic pancreatitis. Surgery to treat chronic pancreatitis tends to be divided into two areas—resectional and drainage procedures. Among the reasons to opt for surgery are if there is a pseudocyst, fistula, ascites, or a fixed obstruction.

3. Pancreatic Fibrosis

Fibrosis is the formation of excess fibrous connective tissue in an organ or tissue in a reparative or reactive process. This can be a reactive, benign, or pathological state. In response to injury, this is called scarring, and if fibrosis arises from a single cell line, this is called a fibroma. Physiologically, fibrosis acts to deposit connective tissue, which can obliterate the architecture and function of the underlying organ or tissue. Fibrosis can be used to describe the pathological state of excess deposition of fibrous tissue, as well as the process of connective tissue deposition in healing.

Fibrosis is similar to the process of scarring, in that both involve stimulated cells laying down connective tissue, including collagen and glycosaminoglycans. Immune cells called macrophages, as well as any damaged tissue between surfaces called interstitium, release TGFβ. There are numerous reasons for this, including inflammation of the nearby tissue, or a generalized inflammatory state, with increased circulating mediators. TGFβ stimulates the proliferation and activation of fibroblasts, which deposit connective tissue. Fibrosis can occur in many tissues within the body, typically as a result of inflammation or damage, and examples include: pancreas (chronic pancreatitis), liver (cirrhosis), lungs (pulmonary fibrosis, Cystic fibrosis, idiopathic pulmonary fibrosis), heart (atrial fibrosis, endomyocardial fibrosis, old myocardial infarction), brain (glial scar), arthrofibrosis (knee, shoulder, other joints), Crohn's Disease (intestine), Dupuytren's contracture (hands, fingers), keloid (skin), mediastinal fibrosis (soft tissue of the mediastinum), myelofibrosis (bone marrow), Peyronie's disease (penis), nephrogenic systemic fibrosis (skin), progressive massive fibrosis (lungs); a complication of coal workers' pneumoconiosis, retroperitoneal fibrosis (soft tissue of the retroperitoneum), scleroderma/systemic sclerosis (skin, lungs), and some forms of adhesive capsulitis (shoulder).

4. Methods of Treating Pancreatitis or Pancreatic Pain Disorder a. Targeting PSCs Pathologically, CP is recognized by significant fibrosis. Pancreatic fibrogenesis is mainly orchestrated by pancreatic stellate cells (PSCs) (Erkan, M., et al., Gut, 2012. 61(2): 172-178; (Omary, M. B., et al., J Clin Invest, 2007. 117(1): 50-59; Pinzani, M., Gut, 2006. 55(1):12-14). During pancreatic damage or disease, quiescent PSCs (qPSCs) undergo activation and transform to proliferative, fibrogenic and contractile myofibroblasts that facilitate collagen deposition and lead to fibrotic tissue. By nature, activated PSCs (aPSCs) are a major target for antifibrotic therapies targeting the pancreas (Omary, M. B., et al., J Clin Invest, 2007. 117(1): 50-59; Apte, M. V., et al., J Gastroenterol Hepatol, 2006. 21 Suppl 3:S97-S101). Therefore, eradication of aPSCs is a logical strategy to prevent, stop and/or reverse fibrogenesis and its complications, pain. Introducing a molecularly-targeted agent that can block qPSC activation in to aPSC and selectively induce apoptosis of aPSCs, not qPSCs, will offer robust antifibrotic effects in CP, because an originator of pancreatic fibrogenesis is depleted. Reversing pancreatic fibrosis stops/reverses CP progress, thus consequently, diminishing CP-associated pain and improving pancreatic functions (FIG. 1).

b. Targeting the PSC-TGFβ Axis with Death Receptor Agonists to Treat Pain.

The transition from acute to chronic pain is an area of active investigation (Reichling, D. B. and Levine, J. D., Trends Neurosci, 2009. 32(12):611-618). Tissue inflammation initiates a cascade of events resulting in peripheral sensitization, i.e., enhancement of the responsiveness of primary afferent neurons (nociceptors), whose bodies are housed in dorsal root ganglia (DRG) and whose central ends synapse with second order neurons in the spinal cord. However, little is known about the driving factors later in inflammation, when tissue fibrosis is prominent. As described herein, treatment of DRG neurons with TGFβ induced changes in excitability and suppressed a specific voltage dependent potassium current (IA), which is a hallmark of nociceptive excitability in chronic pancreatitis (Zhu, Y., et al., Mol Pain, 2012. 8:65). TGFβ can itself sensitize nociceptors, induce pancreatic hyperalgesia, and contribute to the enhanced behavioral response that accompanies CP. As described herein, PSCs upregulate TGFβ during the activation process and affect excitability of DRG neurons. New knowledge about the role of TRAIL and TGFβ in nociception also has implications for other conditions characterized by inflammation and chronic pain—indeed, it has been stated that "The transition from acute to chronic pain states might be the most important challenge in research to improve clinical treatment of debilitating pain." (Reichling, D. B. and Levine, J. D., Trends Neurosci, 2009. 32(12):611-618).

C. Subjects to be Treated

Typically, the subjects to be treated include subjects suffering from, or at risk of suffering from pancreatitis, pancreatic fibrosis, and/or pancreatic pain.

In some embodiments, the subjects to be treated include subjects suffering from, or at risk of suffering from pancreatitis, pancreatic fibrosis, and/or pancreatic pain that also suffer from other chronic or acute conditions, such as type 2 diabetes, liver fibrosis, liver cirrhosis, liver cancer, lung fibrosis, skin fibrosis, pancreatic cancer, metastasized cancer, autoimmune conditions, including type 1 diabetes and rheumatoid arthritis.

In other embodiments, the subjects to be treated include subjects suffering from, or at risk of suffering from pancreatitis, pancreatic fibrosis, and/or pancreatic pain that do not suffer from additional chronic or acute conditions, such as type 2 diabetes, liver fibrosis, liver cirrhosis, liver cancer, lung fibrosis, skin fibrosis, pancreatic cancer, metastasized cancer, autoimmune conditions, including type 1 diabetes and rheumatoid arthritis.

D. Effective Amounts of the DR5 Agonists

The compositions are administered at a dose of 0.001 mg/kg to 100 mg/kg, e.g., 0.001 mg/kg, 0.01 mg/kg, 0.1 mg/kg, 0.5 mg/kg, 1.0 mg/kg, 2.0 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg. For example, the compositions are administered at a dose of between 0.2 mg/kg and 20 mg/kg, or a dose between 0.001 mg/kg and 20 mg/kg.

In some aspects, pancreatic tissues are protected, fibrotic formation is reduced, pancreatic fibrogenesis is reversed, pain is reduced, and healthy pancreatic tissues are unharmed. In one aspect, treating a fibrotic disease or disorder includes reducing pain. Pain is reduced in a subject by 1-100%, e.g., 1%, 5%, 10%, 15%, 20%, 25%, 30%, 40%, 50%, 60%, 70%, 75%, 80%, 90%, 95%, 96%, 97%, 98%, 99%, 99.5%, 99.9%, and 100%.

In one aspect, treating a fibrotic disease or disorder includes reducing pancreatic fibrosis. Pancreatic fibrosis is reduced in a subject by 1-100%, e.g., 1%, 5%, 10%, 15%, 20%, 25%, 30%, 40%, 50%, 60%, 70%, 75%, 80%, 90%, 95%, 96%, 97%, 98%, 99%, 99.5%, 99.9%, and 100%.

In one aspect, treating a fibrotic disease or disorder includes reducing pancreatic inflammation. Pancreatic inflammation is reduced by 1-100%, e.g., 1%, 5%, 10%, 15%, 20%, 25%, 30%, 40%, 50%, 60%, 70%, 75%, 80%, 90%, 95%, 96%, 97%, 98%, 99%, 99.5%, 99.9%, and 100%.

1. Dosage and Treatment Regimes for Combination Therapies

The methods of treatment typically include treatment of a disease or symptom thereof, or a method for achieving a desired physiological change, including administering to a a mammal, especially a human being, an effective amount of a pro-apoptotic agent to treat pancreatitis or symptom thereof, or to produce the physiological change.

The effective amount of a death receptor agonist may be administered as a single dose once, or multiple times, to the subject. The administration may be once daily, twice daily, trice daily, once weekly, twice weekly, biweekly, or once monthly.

The effective amount of a death receptor agonist can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days.

In some embodiments, the unit dosage is administered as the main therapy. In other embodiments, the unit dosage is administer together with a second agent in a combination therapy.

a. Combination Therapies

In some embodiments, the death receptor agonist is in combination with an additional active agent. The death receptor agonists and the additional active agent can be administered together, such as part of the same composition, or administered separately and independently at the same time or at different times (i.e., administration of the ligand or agonist and the second active agent is separated by a finite period of time from each other). Therefore, the term "combination" or "combined" is used to refer to either concomitant, simultaneous, or sequential administration of the ligand or agonist and the second active agent. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

In some embodiments, administration of the death receptor agonists in combination with the second active agent achieves a result greater than when the pro-apoptotic agent and the second active agent are administered alone or in isolation (i.e., the result achieved by the combination is more than additive of the results achieved by the individual components alone). In some embodiments, the effective amount of one or both agents used in combination is lower than the effective amount of each agent when administered separately. In some embodiments, the amount of one or both agents when used in the combination therapy is sub-therapeutic when used alone.

A treatment regimen of the combination therapy can include one or multiple administrations of ligand or agonist. A treatment regimen of the combination therapy can include one or multiple administrations of the second active agent.

In some embodiments, the pro-apoptotic agent is administered prior to the first administration of the second active agent. In other embodiments, the ligand or agonist is administered after to the first administration of the second active agent.

The ligand or agonist can be administered at least 1, 2, 3, 5, 10, 15, 20, 24 or 30 hours or days prior to or after administering of the second active agent.

Dosage regimens or cycles of the agents can be completely, or partially overlapping, or can be sequential. For example, in some embodiments, all such administration(s) of the pro-apoptotic agent occur before or after administration of the second active agent. Alternatively, administration of one or more doses of the pro-apoptotic agent can be temporally staggered with the administration of second therapeutic agent to form a uniform or non-uniform course of treatment whereby one or more doses of pro-apoptotic agent are administered, followed by one or more doses of second active agent, followed by one or more doses of death receptor agonists; or one or more doses of second active agent are administered, followed by one or more doses of the pro-apoptotic agent, followed by one or more doses of second active agent; etc., all according to whatever schedule is selected or desired by the researcher or clinician administering the therapy.

V. Kits

Medical kits are also disclosed. The medical kits can include, for example, a dosage supply of a pro-apoptotic agent, preferably a ligand or agonist for an agonistic TRAIL receptor, alone or in combination with a second therapeutic agent. When in combination with a second therapeutic agents, the active agents can be supplied alone (e.g., lyophilized), or in a pharmaceutical composition (e.g., an admixture). The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

The present invention will be further understood by reference to the following non-limiting examples. The contents of all references, patents, and published patent applications cited throughout this application, as well as the figures, are incorporated herein by reference.

EXAMPLES

General Methods

To test the efficacy of TRAIL$_{PEG}$ in vivo, biological samples were analyzed as follows.

Blood Chemistry and Hepatic Lipid Levels:

Serum amylase, lipidase, ALT, AST, ALP, sodium, cholesterol, triglyceride, glucose, albumin, protein and urea nitrogen levels are determined using the IDEXX analyzer.

Histology and IHC:

Fixed pancreatic samples were stained with H&E, Sirius Red, α-SMA and counterstained with Mayer's hematoxylin. Immunofluorescence (IF) double staining was performed using appropriate antibodies against α-SMA, active caspase-3, and nuclei were stained with DAPI. TUNEL assay on pancreatic tissues was also performed to determine DNA damage from apoptotic signaling cascades.

Real-Time PCR:

The expression levels of genes was measured by RT-PCR (ABI7500) using appropriate primers for: DR5, α-SMA, Pdgf-r, Col1a1, Col1a2, Col1a3, Tgf-b1, Tgf-br2, Tgf-br3, Bmp7, Timp1/3, Mmp2/3/7/9/13 as well as Bcl-2, Bcl-xl, Mcl-1, FLIP, and cIAP.

Western Blotting:

Western blot analyses were performed on protein extracts from pancreas homogenates for key markers including, but not limited to, DR5, α-SMA, collagen, Timp, Tgfβ, Mmps, caspase-8/-9/-3, cleaved PARP-1, Bcl-2, Bcl-xl, Mcl-1, FLIP, FADD, and t-Bid.

Pain Behavior Using VFF Testing and Electrical Stimulation:

After TRAIL$_{PEG}$ treatment, 4 rats from each EtOH/cerulein/LD diet-induced CP group were used for VFF testing and electrical stimulation studies.

Data and Statistical Analysis:

Six to ten animals per group for antifibrotic therapy and four animals per group for anti-pain therapy were needed to observe a difference between the mean values of treated and control groups for a 5% significance level and 90% power. Tissue slides were analyzed by pathologists without prior knowledge of the sample. Staining intensity and extent were graded on an accepted scoring system among 0-4. Immunohistochemistry (IHC) images were analyzed by NIH Image J. Comparisons between control and up/down-regulated receptors, biomarkers and among groups with and without TRAIL$_{PEG}$ treatment were performed by two-tailed Fisher's exact test, one way ANOVA or the chi-square test, as appropriate. All data sets were analyzed by multiple comparisons among the various treatment groups. All analyses are performed using Prism software (GraphPad). P values less than 0.05 are considered statistically significant in all analyses.

Example 1. TRAIL$_{PEG}$ Effect on Pancreatic Cells

PEGylation is the gold standard to extend half-life ($t_{1/2}$) of protein drugs and a highly efficient commercial strategy (Harris et al., Nat Rev Drug Discov, 2(3):214-221 (2003)). More than ten PEGylated biologics are FDA-approved and PEGylated proteins are generally considered less immunogenic (Alconcel et al., Polymer Chemistry, 2(7):1442-1448 (2011)). Extremely short $t_{1/2}$ of TRAIL (less than 5 min in rodents and 30 min in humans) (Kelley et al., J Pharmacol Exp Ther, 299(1):31-38 (2001); Ashkenazi et al., J Clin Oncol, 26(21):3621-3630 (2008)) makes it difficult to study TRAIL function and validate the drug efficacy particularly in vivo. PEGylated TRAIL was produced by stabilizing a trimeric TRAIL, inclusion of an isoleucine-zipper amino acid motifs (iLZ) at the end terminal of each monomer that favor trimer formation at the N-terminus, with a 5 kDa PEG molecule (TRAIL$_{PEG}$) (WO 2007/145457). TRAIL$_{PEG}$ significantly improved stability and longer circulation half-lives in rats and monkeys vs. recombinant TRAIL like Dulanermin (Genentech), (Lemke, J., et al., Cell Death Differ, 2014. 21(9):1350-1364) which was investigated in the clinic and showed a good safety profile but low efficacy.

Materials and Methods

To investigate the potential for pancreas toxicity, TRIAL$_{PEG}$ was tested in pancreatic acinar cells (AR42J, ATCC CRL-1492) (ATCC) and primary human islets (pancreas) (Celprogen, Torrance, Calif.). AR42J cells (ATCC) were maintained in RPMI 1640 medium (Corning cellgro, Manassas, Va., USA) supplemented with 20% fetal bovine serum (FBS; Sigma, St Louis, Mo.), 100 U/ml penicillin/streptomycin (Life Technology). Human Pancreatic Islets of Langerhans cells (#35002-04, Celprogen, Torrance, Calif.) were maintained in Human Pancreatic Islets of Langerhans primary cell culture complete extracellular Matrix (#E35002-04, Celprogen) and media with serum (Celprogen #M35002-045). Cells were cultured at 37° C. under a humidified atmosphere of 5% $CO_2$. Briefly, $2\times10^4$ cells were cultured for 24 h in a 96-well plate and then treated with TRAIL$_{PEG}$ (0, $10^1$, $10^2$, $10^3$ ng/mL) for 3 h and cell viability was analyzed by cell death MTT assay. After incubation, MTT solution was added to each well and incubated for 4 hours. The absorbance at 430 nm was determined using a microplate reader (Bio-Tek Instruments Inc, Winooski, Vt.).

Results

Figure 2:
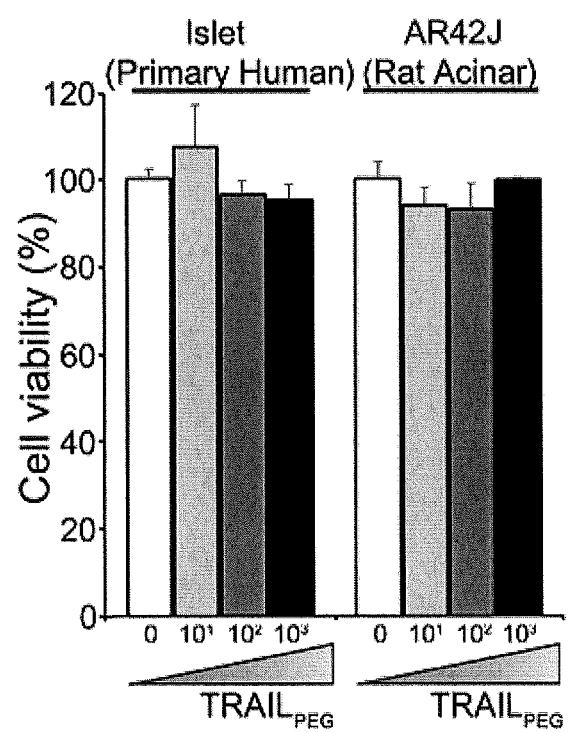
FIG. 2 is a bar graph showing percent cell viability (%) of primary human islets and rat acinar cells when the cells are treated with 10, 100, 1,000 ng/mL of $TRAIL_{PEG}$. No toxicity against normal pancreatic cells, including primary human islets and pancreatic acinar cells was detected. $TRAIL_{PEG}$ (10, 100, 1,000 ng/mL) was incubated with various cells for 24 hours and cell death was quantified by MTT assays.

As shown in FIG. 2, TRAIL$_{PEG}$ did not show any toxicity on acinar cells (AR42J) and primary human islets.

Example 2: Culture-Activated Pancreatic Stellate Cells Become Sensitive to TRIAL-Induced Apoptosis The results show that when primary human PSCs were culture-activated, PSCs transform to myofibroblast-like cells and upregulate DR4 and DR5 as well as other fibrogenic markers and become highly sensitive to TRAIL$_{PEG}$ through upregulated DR5/DR4.

Activated Primary Human PSCs (aPSCs), not Quiescent PSCs (qPSCs), Upregulate DRs and Become Sensitive to TRAIL-Mediated Apoptosis.

Materials and Methods

TRAIL-induced apoptosis in primary human PSCs was tested. Human PSCs (ScienceCell Research Lab) were grown in SteCM medium (ScienceCell) supplemented with 2% of FBS, 1% of stellate cell growth supplement and 1% of penicillin/streptomycin solution according to the manufacturer's instructions. $2\times10^5$ PSCs were cultured in 6-well plates coated with poly-L-lysine and cultured for 2 days (quiescent) and 7 days (activated) and harvested for analysis. Unlike other cells, stellate cells including hepatic stellate cells (HSCs) and pancreatic stellate cells (PSCs) can be activated and differentiated into activated stellate cells with culture of successive generations (e.g. culturing for over 5 days). Expressions of DR5 and DR4, α-SMA, collagen and TGFβ as well as PDGFR and TGFβ were analyzed by western blotting at quiescent and activated cell states. Just culturing for 7 days induces activation.

Results

Figure 3A:
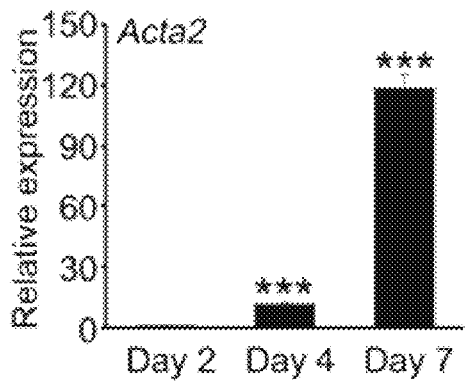
FIGS. 3A, 3B, 3C, 3D, 3E, and 3F are bar graphs showing relative expression of the indicated genes by culture-activated primary human PSCs at days 2, 4, and 7 of culture. The culture-activated primary human PSCs upregulate Acta2 (α-SMA, activated stellate cells marker), fibrogenic markers and TRAIL receptors (DR5/DR4) and become highly sensitive to TRAIL-induced apoptosis. The qPCR analysis of quiescent (Day 2) and activated PSCs (Day 4 and Day 7). *$P<0.05$, $P<0.01$, *$P<0.001$ vs. Day 2.
Figure 3B:
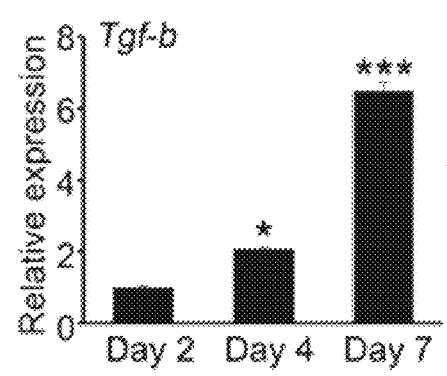
Figure 3C:
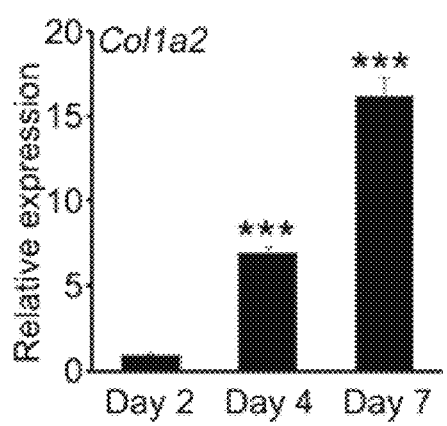
Figure 3D:
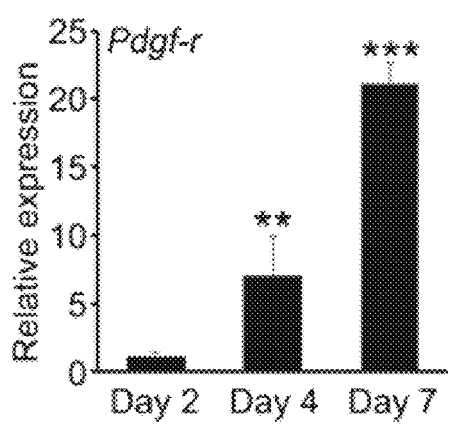
Figure 3E:
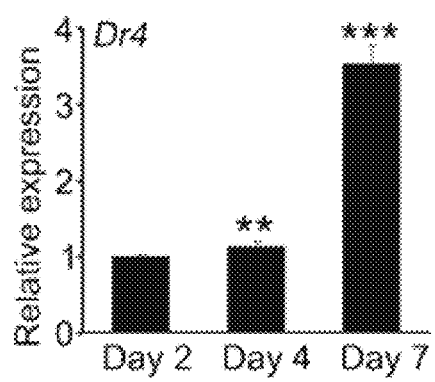
Figure 3F:
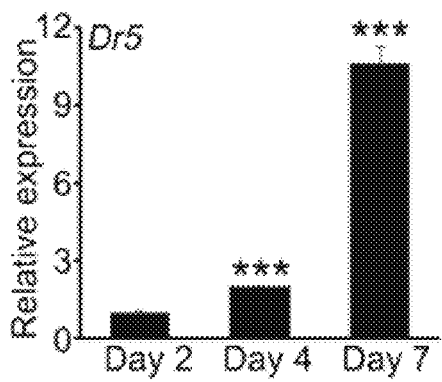
Figure 4:
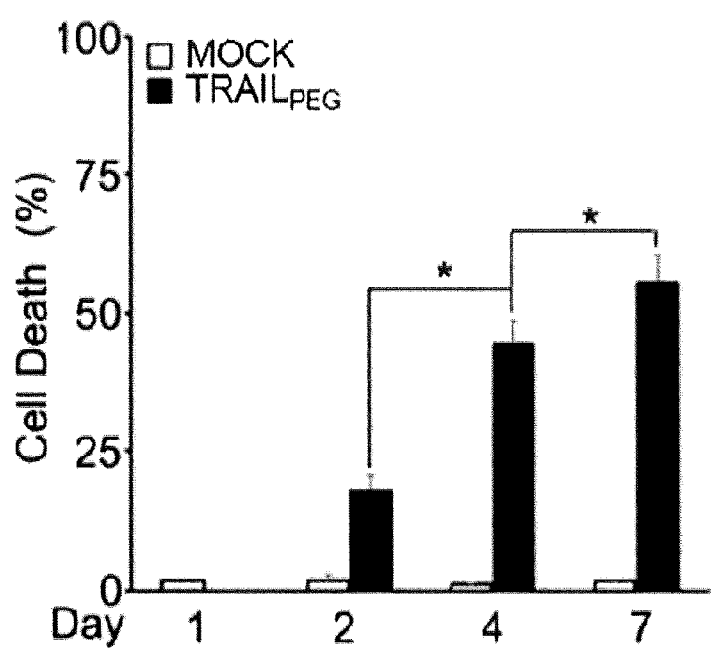
FIG. 4 is a bar graph showing percent cell death (%) in culture-activated primary human PSCs at days 1, 2, 4, and 7 of culture. *$P<0.05$

Activation induced morphological changes of PSCs and significantly upregulated fibrogenic markers and importantly DR4 and DR5 (FIGS. 3A-3F). When the cells were treated with TRAIL$_{PEG}$ (1 µg/mL) for 3 hours in quiescent or activated states, TRAIL-induced apoptosis was clearly observed in aPSCs but not in qPSCs as evidenced by cell apoptosis features and quantified cell death measured by an MTT assay (FIG. 4).

Monitoring Regulation of TRAIL Signaling Molecules, Fibrosis Markers and Apoptosis Markers.

The regulation of TRAIL signaling molecules, fibrosis markers and apoptosis markers were monitored in primary human PSCs during activation. The safety was confirmed in primary human islets and pancreatic acinar cells.

Materials and Methods

Representative TRAIL signaling and fibrosis-related molecules were screened at protein and mRNA levels in primary human PSCs (ScienceCell). PSCs were culture-activated for 2, 4, and 7 days in SteCM medium and harvested. The expression of TRAIL signaling molecules DR5, DR4, and FLIP and fibrosis markers α-SMA, Pdgf-r, collagen type-1/2/3, Mmps, Timps, Collagens, and TGFβ, and apoptotic and anti-apoptotic markers including caspase-8, -9, -3, cleaved PARP-1, BCL-2, BCL-XL, FLPI, and cIAP, were analyzed by qPCR and western blotting. Changes in PSC morphology were observed by microscopy. Once the expression patterns of TRAIL signaling molecules was confirmed, the effect of TRAIL-induced apoptosis during PSC activation was investigated. For molecular studies, quiescent and culture-activated PSCs (from 2 to 7 days) were treated with TRAIL$_{PEG}$ at 1 µg/mL. Activated PSCs were treated with or without TRAIL$_{PEG}$ (1 µg/mL) for 3 hours and analyzed by qPCR.

Results

Activated PSCs upregulated multiple anti-apoptotic proteins such as BCL-2, BCL-XL, X-IAP, but the cells remained sensitive to TRAIL-induced apoptosis as evidenced by the upregulated cleaved (Cl) PARP-1, Cl Casep-8 and Cl Casp-3. In the case of most primary cancer cells, such upregulated anti-apoptotic proteins strongly inhibit TRAIL-induced cell death, causing TRAIL resistance. It was also shown that activated PSCs are difficult to kill when incubated with conventional toxic agents including cancer drugs like doxorubicin (DOX, 100 nM), cisplatin (CIS, 10 µM), or hydrogen peroxide (H$_2$O$_2$, 10 µM). When activated PSCs were incubated with TRAIL$_{PEG}$ (1 µg/mL) for 3 hr and the toxic agents for 48 hr, only TRAIL$_{PEG}$ induced strong apoptosis, as TRAIL$_{PEG}$-treated cells upregulated Cl PARP-1, Cl Casp-8, Cl Casp-3 and Cl Casp-9.

The culture-activated primary human PSCs upregulate multiple anti-apoptotic proteins (BCL-XL, BCL-2, X-IAP) but remain sensitive to TRAIL-induced apoptosis as evidenced by upregulated cleaved (Cl) PARP-1, Cl Casp-8 (caspase-8), and Cl Casp-3 (caspase-3).

Example 3: Anti-DR5 Antibody, but not Anti-DR4 Antibody, Induces Selective Apoptosis in Activated Pancreatic Stellate Cells TRAIL induces apoptosis by binding to its cognitive receptors, DR4 and DR5. To investigate whether both TRAIL receptors are necessary to induce apoptosis in activated PSCs, the caspase 3/7 activity (apoptosis markers) was measured by treating activated PSCs with either human anti-DR4 agonistic antibody (mapatumumab) or anti-DR5 agonistic antibody (conatumumab). For DR4 or DR5 specific antibody treatments, PSCs were culture activated for 7 days on 96 well plate (Corning) and sequential concentrations (0, 10$^1$, 10$^2$, 10$^3$ ng/mL) of mapatumumab (human anti-DR4 antibody, Creative Biolabs) or conatumumab (human anti-DR5 antibody, Creative Biolabs) with Protein G (Thermo Fisher Scientific, Waltham, Mass. #21193) were added and incubated for 3 h and the cells tested for caspase activity. Caspase 3/7 activities were measured by caspase3/7 assay kit (Promega) according to the manufacturer's protocol. The luminescence of each sample was measured on a plate reader (Bio-Tek Instruments Inc) with parameters of 1 min lag time and 0.5 sec/well read time (n=4).

To investigate the DR4 and DR5 expression profiles on the cellular membrane of activated PSCs, human primary PSCs were culture-activated for 2 and 7 days, cells were harvested, washed twice with cold PBS and incubated for 30 min with Anti-Human CD261 (DR4)-PE or Anti-Human CD262 (DR5)-PE (eBioscience, San Diego, Calif.). Mouse IgG1 K Isotype Control PE (eBioscience) was used as an isotype control. Cell surface expression of TRAIL receptors was analyzed by flow cytometry (Accuri C6, BD Biosciences, San Jose, Calif.). Histographical and mean fluorescence intensity (MFI) data were analyzed by using FlowJo software (FlowJo LLC, Ashland, Oreg.).

Results

Figure 5:
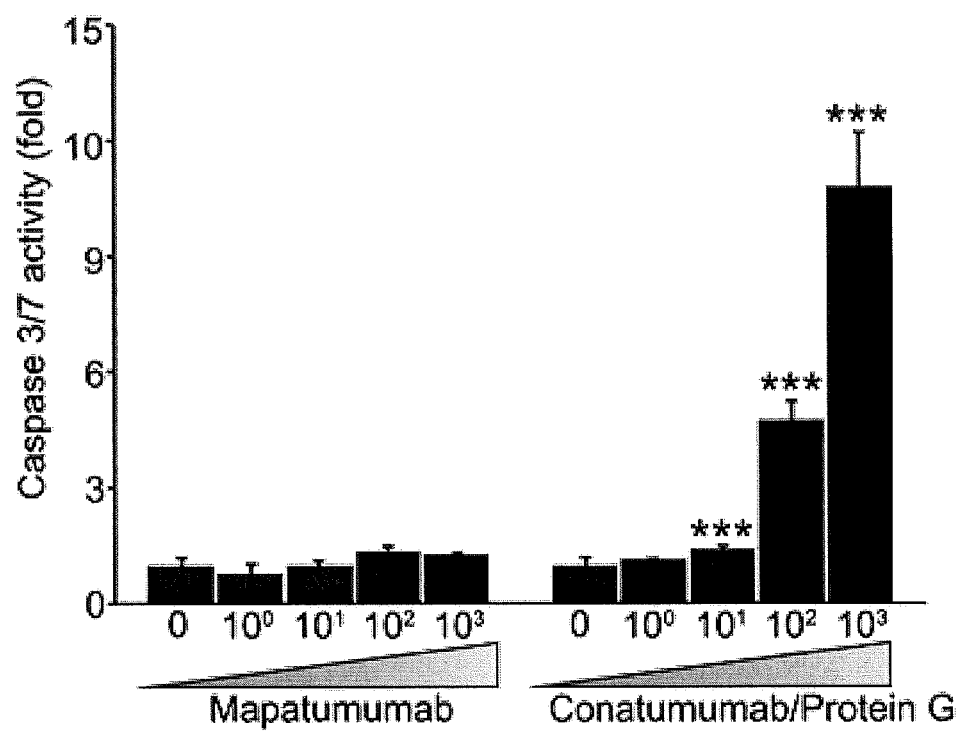
FIG. 5 is a bar graph showing caspase 3/7 (apoptosis maker) activity change (fold) culture-activated PSCs were treated with indicated concentrations of Mapatumumab (anti-DR4 agonistic antibody, 0-$10^3$ ng/mL) or Conatumumab (anti-DR5 agonistic antibody, 0-$10^3$ ng/mL). Only conatumumab induces apoptosis in activated PSCs. This indicates that DR5, but not DR4, plays critical roles in TRAIL signaling in activated stellate cells. ***$P<0.001$ vs. non-treated PSCs.

As shown in FIG. 5, when activated PSCs were treated with conatumumab (DR5 antibody, 10$^3$ ng/mL), caspase-3/7 activity was increased by 10.79±1.42-fold. In contrast, mapatumumab (10$^3$ ng/mL) did not increase caspase-3/7 activity (1.27±0.03-fold). Next, expressions of DR4 and DR5 on the cellular membrane of PSCs was investigated by flow cytometry analysis using DR4 or DR5 specific antibodies labeled with phycoerythrin (PE) in quiescent (Day 2) and activated PSCs (Day 7). Unexpectedly, a large shift in the mean fluorescence intensity (MFI) was observed only in DR5 antibody treated activated PSCs compared to that of DR4 antibody (FIGS. 6A and 6B). This result showed that DR5 is predominantly expressed on the cell surface of activated PSCs. Taken together, it is shown that TRAIL-induced apoptosis in activated PSCs is predominantly mediated by DR5 and not by DR4.

Example 4: Alcohol-Activated Pancreatic Stellate Cells Become Sensitive to TRAIL-Induced and Anti-DR5 Antibody-Induced Apoptosis A major cause of chronic pancreatitis (in approximately 70% of all cases) is alcohol abuse. It is shown that quiescent PSCs, when activated by alcohol, ethanol (EtOH), significantly upregulate TRAIL receptors DR4 and DR5 and become sensitive to TRAIL-induced apoptosis.

Materials and Methods

To investigate the effect of alcohol on PSC activation, 2×10$^5$ human primary PSCs were cultured in 6-well plates coated with poly-L-lysine and cultured for 24 h and treated with ethanol (EtOH) (0, 30, 50 mM) for 48 h. After alcohol stimulation, the cells were harvested for real-time qPCR analysis and western blotting. The expression of TRAIL signaling molecules including DR4, DR5 and fibrogenic factors including a-SMA (Acta2), collagens, are analyzed. To investigate TRAIL-induced apoptosis in alcohol-activated PSCs, 2×10$^4$ cells were cultured for overnight in a 96-well plate and then activated with 50 mM EtOH for 48 h. EtOH-activated PSCs were treated with various concentrations (0, $10^1$, $10^2$, $10^3$ ng/mL) of TRAIL, $TRAIL_{PEG}$, mapatumumab (human anti-DR4 antibody) or conatumumab (human anti-DR5 antibody) and incubated for 3 h. Apoptosis was measured by MTT cell death assay and caspase 3/7 assay as described above.

Results

Figure 8A:
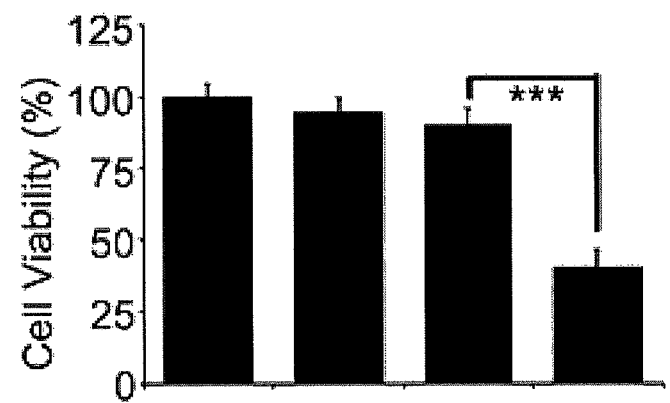
FIGS. 8A and 8B are bar graphs showing cell viability (%) as quantified by MTT assay and caspase 3/7 activity (apoptosis maker) relative ratios after treating EtOH (50 mM)-activated PSCs with $TRAIL_{PEG}$ (1 μg/mL). Only alcohol-activated PSCs are sensitive to TRAIL-induced cell death. $P<0.01$, *$P<0.001$ vs. non-EtOH activated PSCs.
Figure 8B:
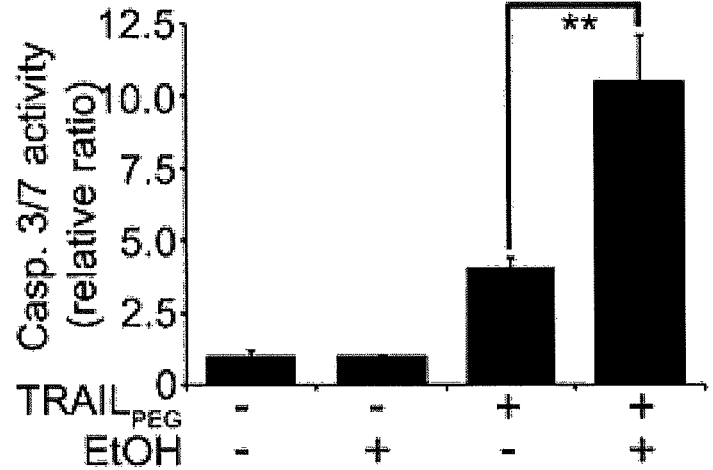

As shown in FIGS. 7A-7E, quiescent PSCs treated with EtOH (50 mM) for 48 hours continuously up-regulated the mRNA levels of α-SMA (Acta2, 3.7.5±0.29 fold), collagen, (Col1α2, 4.0±0.43 fold), PDGF receptor (Pdgf-r, 1.9±0.25 fold) as well as TRAIL receptors (DR4; 2.1±0.12, DR5, 1.8±0.0.09 fold) compared to non-activated PSCs. In addition, PSCs activated by EtOH (50 mM) demonstrated significantly increased cell death against $TRAIL_{PEG}$ (59.95±6.37% cell death) and caspase 3/7 activity (apoptosis marker, 10.45±1.60-fold) compared to that of non-activated PSCs (FIGS. 8A and 8B).

Figure 9:
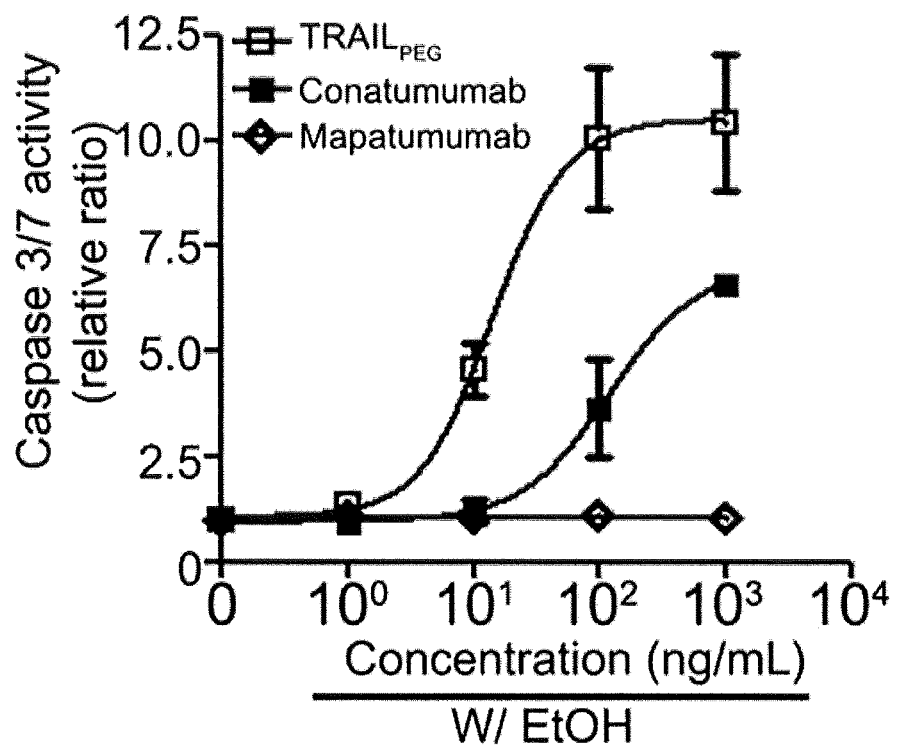
FIG. 9 is a line graph showing quantified caspase 3/7 activity (apoptosis maker) after treating EtOH (50 mM)-activated PSCs with various concentrations of $TRAIL_{PEG}$, Conatumumab (anti-DR5 agonistic antibody) and Mapatumumab (anti-DR4 agonistic antibody). Only $TRAIL_{PEG}$ and conatumumab induce apoptosis in EtOH-activated PSCs.
Figure 10A:
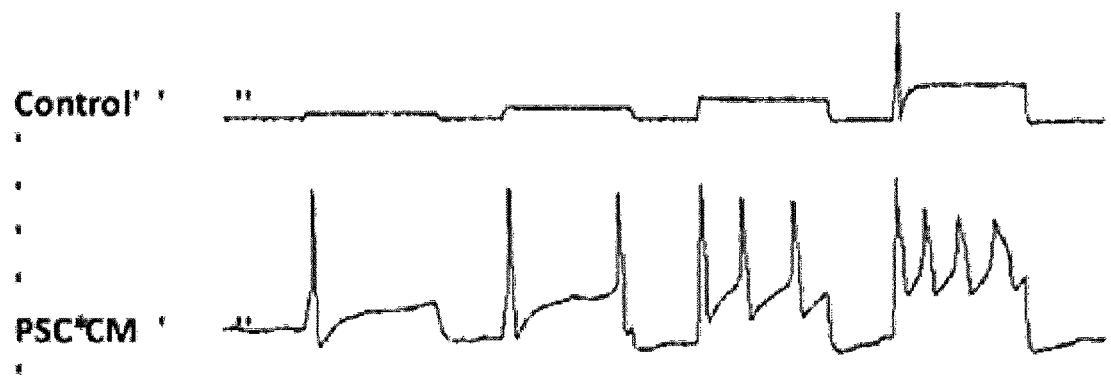
FIGS. 10A-10E show the effects of a 48 hour incubation in culture with conditioned medium (CM) obtained from activated PSCs in serum free conditions (PSC-CM) on the excitability of sensory neurons from dorsal root ganglia (DRG) in vitro, as demonstrated by whole-cell patch-clamp recording.
Figure 10B:
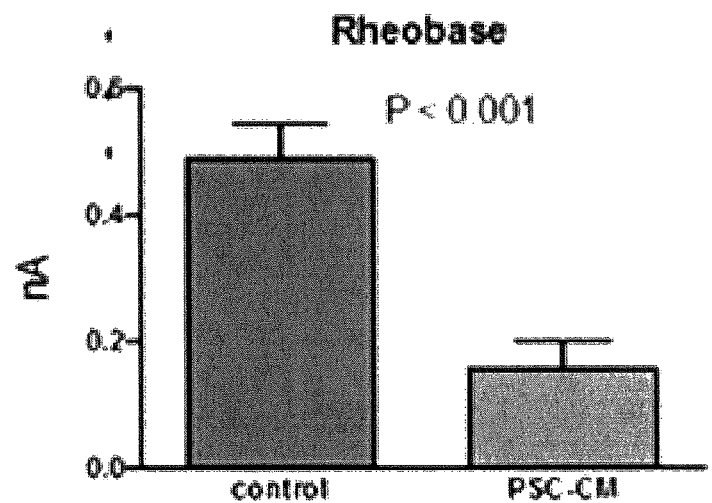
Figure 10C:
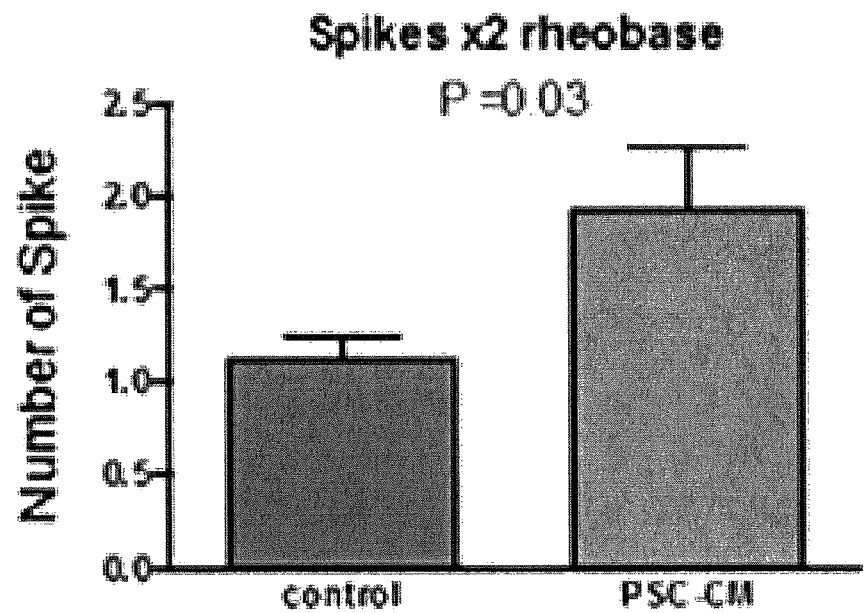
Figure 10D:
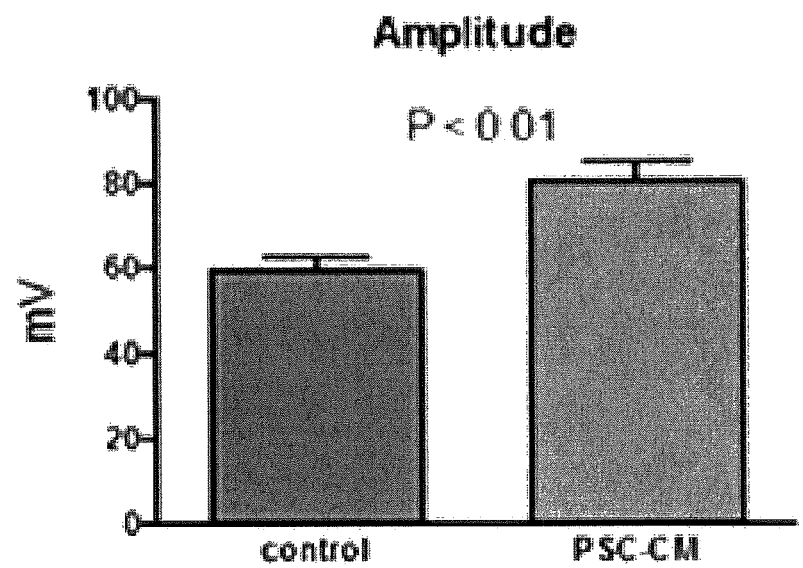
Figure 10E:
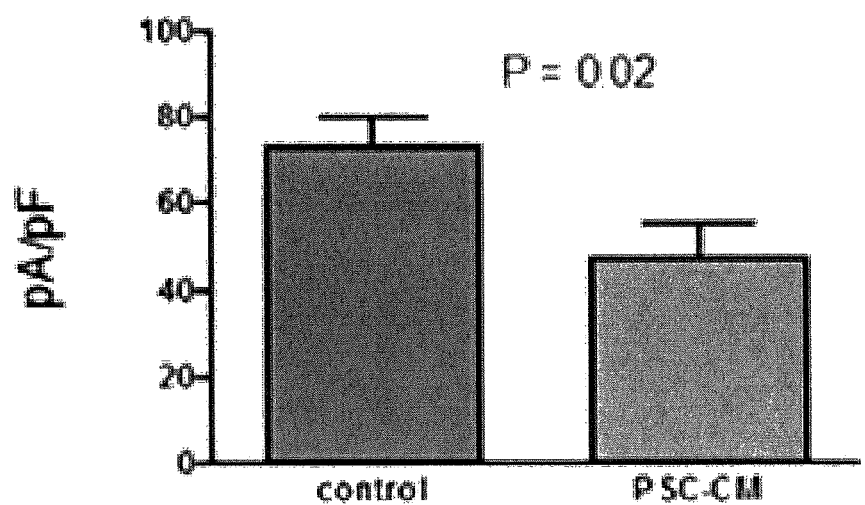

When alcohol-activated PSCs were treated with different concentrations of $TRAIL_{PEG}$, contumumab (anti-DR5 agonistic antibody) and maptumumab (anti-DR4 agonistic antibody) while alcohol was still present in culture, only $TRAIL_{PEG}$ and contumumab induced strong apoptosis dose-dependently (FIG. 9). As described in Example 3, maptumumab, anti-DR4 antibody, did not induce any toxicity in alcohol-activated PSCs. The studies demonstrate that only anti-DR5 agonistic antibodies induce apoptosis in activated pancreatic stellate cells. Human TRAIL and $TRAIL_{PEG}$ bind to both DR4 and DR5, but antibodies bind to only either DR4 or DR5. These results confirm that human TRAIL analogs and anti-DR5 agonistic antibodies are useful for the treating pancreatic fibrosis, pain and pancreatitis by targeting upregulated DR5 in the pancreas.

Example 5: The Anti-Nociceptive Role of TRAIL Signaling on the PSC-Nociceptor-TGFβ Axis It is shown that activated PSCs upregulate TGFβ (FIG. 3B). Therefore, activated PSCs could be the dominant cellular source for TGFβ and play a role in nociceptive sensitization in pain.

Materials and Methods

The effect of activated PSCs on the excitability of sensory neurons from DRG (dorsal root ganglia) in vitro was tested by incubating isolated rat DRGs with conditioned medium obtained from culture-activated PSCs (7 days) in serum-free conditioned medium (PSC-CM). The excitability was accessed by whole-cell patch-clamp electrophysiological recording with Axopatch 200B amplifier and digitized with a Digidata 1200.

Results

Figure 16:
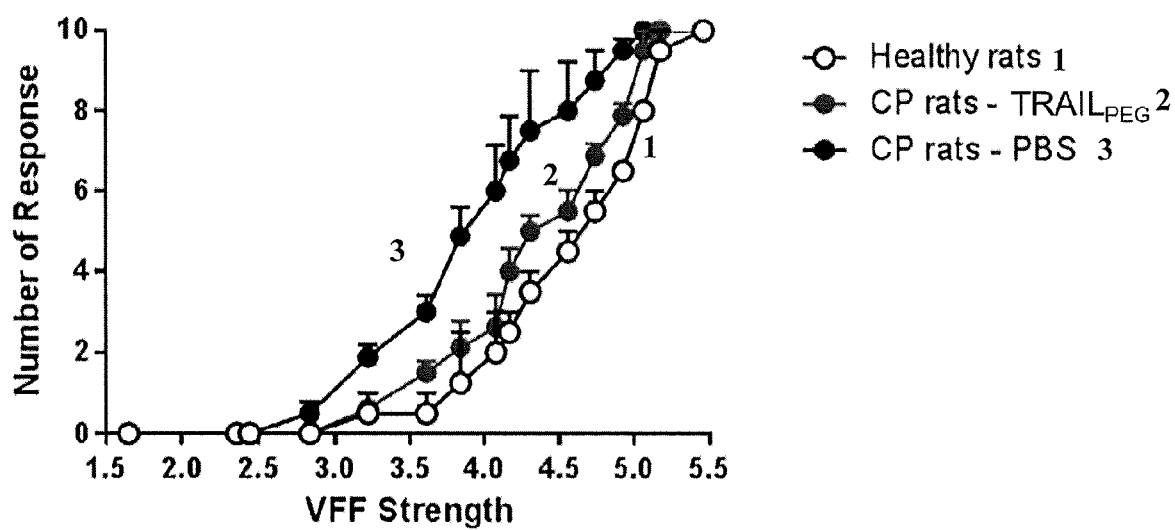
FIG. 16 is a line graph showing number of response versus VFF strength in healthy and CP rats (EtOH-CP) treated with PBS or TRAIL$_{PEG}$. TRAIL$_{PEG}$ reduces pancreatitis-associated pain. The effects of TRAIL$_{PEG}$ on nociception was assessed in chronic pancreatitis (CP) rat models by measuring mechanical sensitivity of the abdomen by VFF (Von Frey filament) method. TRAIL$_{PEG}$ shows strong anti-nociceptive efficacy in CP models.

As demonstrated in FIGS. 10A-10E, PSC-CM caused a significant and comparable response from DRG, indicating that PSC activation plays critical roles in nociceptor sensitization. $TRAIL_{PEG}$-treatment reversed pain as demonstrated in a chronic pancreatitis models (FIG. 16, Example 6). Therefore, activated PSCs sensitized nociceptors via production of TGFβ and promoted hyperalgesia, which was blocked by $TRAIL_{PEG}$.

Example 6: Utilizing $TRAIL_{PEG}$ for Antifibrotic and Anti-Pain CP Therapy

To confirm that death receptors are a valuable target for antifibrotic and anti-pain therapies and diagnosis, the efficacy of $TRAIL_{PEG}$ as a potent antifibrotic, anti-pain, drug was investigated. $TRAIL_{PEG}$ showed strong antifibrotic efficacy in both acute (FIG. 11) and chronic pancreatitis (FIGS. 13A-15). Its anti-pain efficacy was demonstrated in a rat CP model (FIG. 16). The study demonstrates that systemically administered $TRAIL_{PEG}$ ameliorates both acute pancreatitis (AP) and chronic pancreatitis (CP) in animal models and causes a decline in somatic referred hyperalgesia in CP models.

Materials and Methods

Acute pancreatitis (AP) was induced by hourly intraperitoneal injections of 20 μg/kg cerulein in rats (220-240 g) four times and treated with PBS or $TRAIL_{PEG}$ (i.v., 4 mg/kg, single injection) 2 hr after the last injection of cerulein. Two control groups were treated with PBS or $TRAIL_{PEG}$ without cerulein. AP rats were sacrificed at 24 hr after $TRAIL_{PEG}$ treatment.

Figure 12:
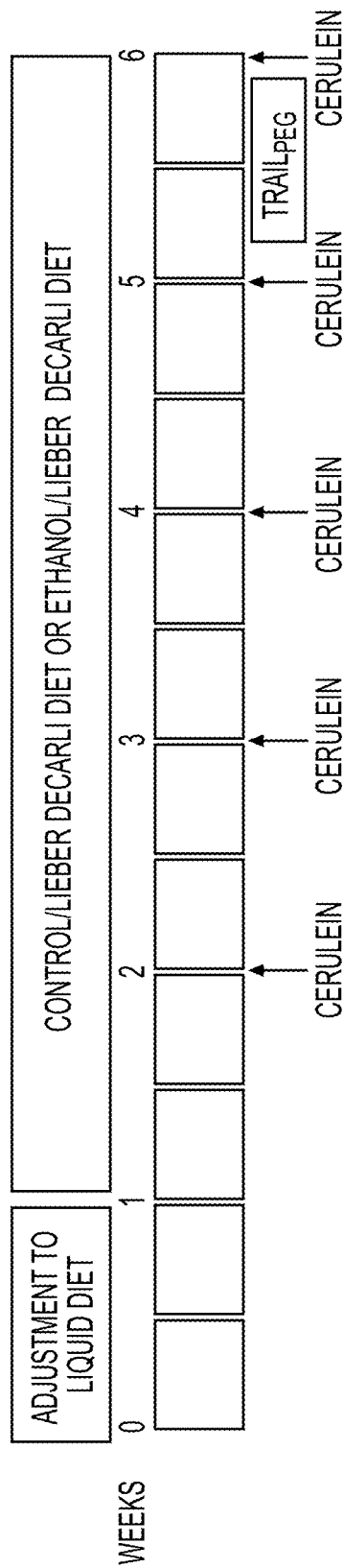
FIG. 12 is a diagram depicting a timeline for the study design for testing TRAIL$_{PEG}$ in a chronic pancreatitis (CP) rat model. A model of alcohol-induced CP was established by feeding SD rats an ethanol/Lieber DeCarli liquid diet for 43 days and five weekly injections of cerulein (20 µg/kg). Ethanol was supplemented into the diet from 0 to 36% of total calories for one week and maintained at a final ethanol concentration starting at day 7 to end of the study. Rats were treated with cerulein (four hourly i.p. injections) on day 14, 21, 28, 35, and 41. TRAIL$_{PEG}$ (4 mg/kg, i.v.) or PBS (control) was treated daily for 7 days beginning on day 36.
Figure 13A:
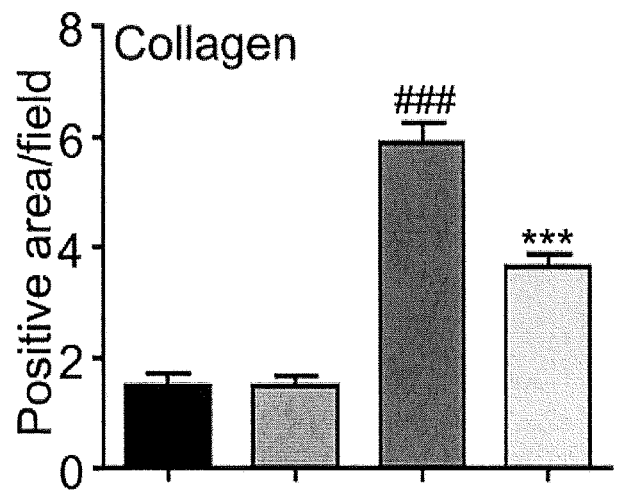
FIGS. 13A and 13B are bar graphs showing positive area/filed as a quantification from digital images of Masson's trichrome (collagen staining) and a-SMA (activated PSCs marker) stain.
Figure 13B:
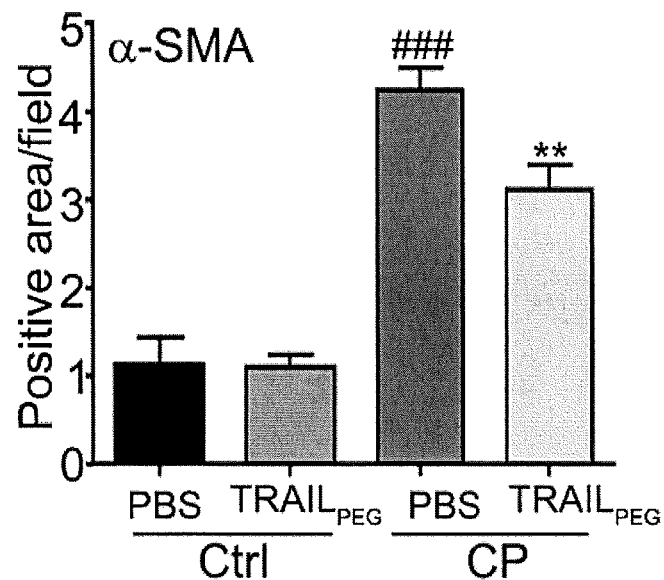
Figure 14A:
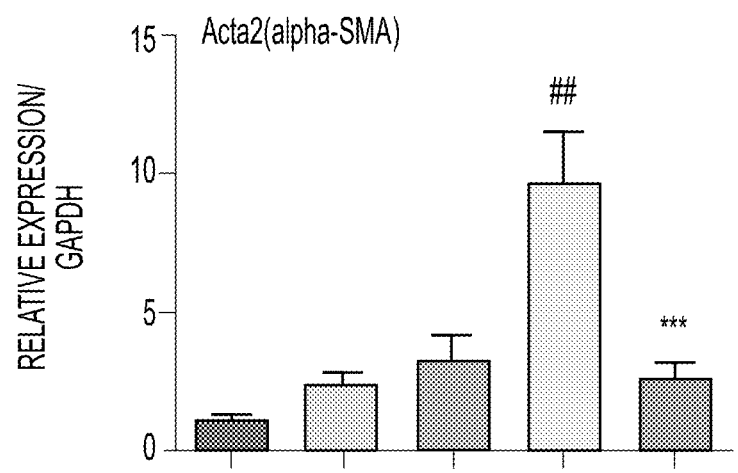
FIGS. 14A-14I are bar graphs showing the indicated gene expression relative to GAPDH in cerulein- and ethanol/Lieber DeCarli diet-induced CP rats (EtOH-CP) treated with PBS or TRAIL$_{PEG}$. The effect of TRAIL$_{PEG}$ on multiple fibrogenic markers is shown. TRAIL$_{PEG}$ down-regulates multiple fibrosis-associated molecules at mRNA (gene) levels in cerulein- and ethanol/Lieber DeCarli diet-induced CP rats (EtOH-CP). The gene expression levels of fibrosis-associated markers including: a-SMA, Collagen1, Collagen3, PDGFr, TIMP1, TIMP3, Fibronectin, Pap, and TGFβ were all reduced after treatment with TRAIL$_{PEG}$. Acta2 is the mRNA name for alpha-SMA. TIMP is an inhibitor of MMP (MMP's are responsible for degradation of collagen). Fibronectin is a fibrosis marker. ##$P<0.01$, ###$P<0.001$ vs. Pair Fed (control), *$P<0.05$, $P<0.01$, *$P<0.001$ vs. EtOH-CP/PBS.
Figure 14B:
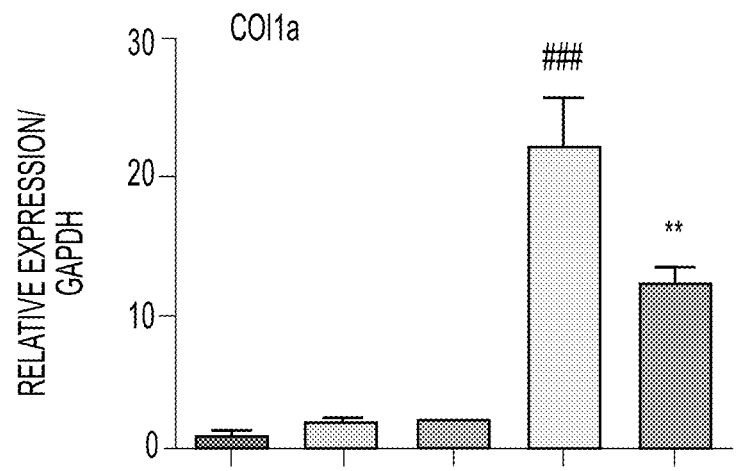
Figure 14C:
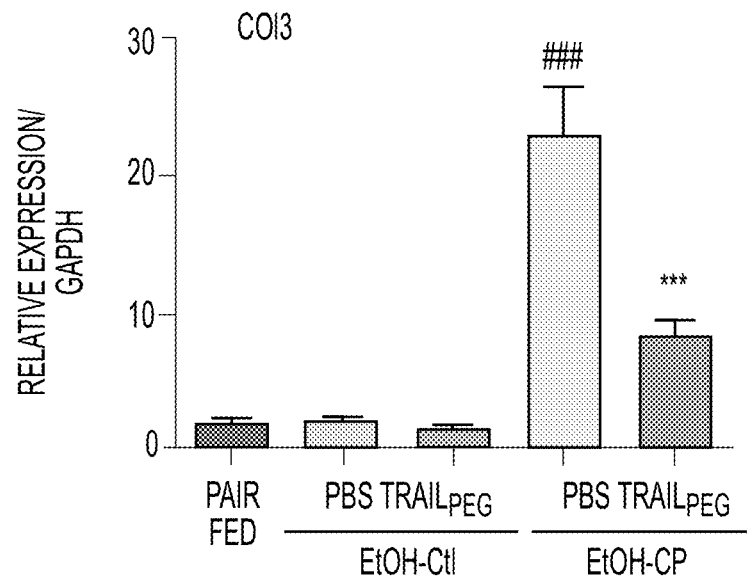
Figure 14D:
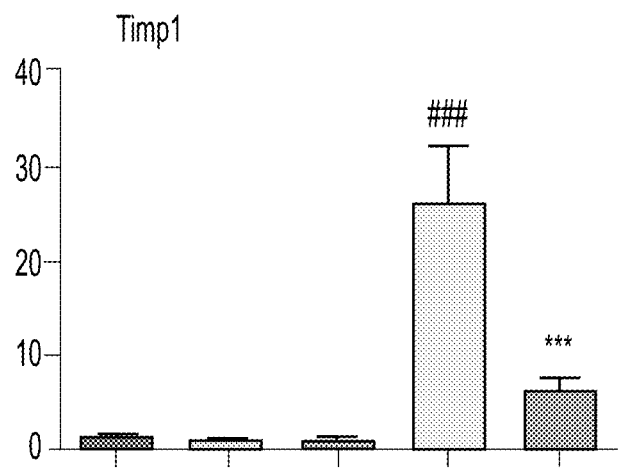
Figure 14E:
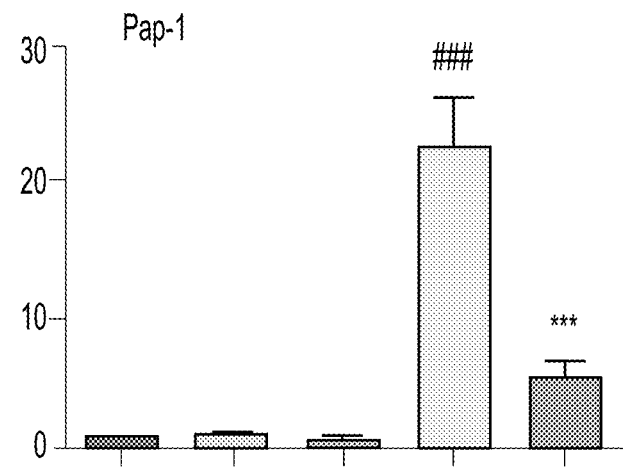
Figure 14F:
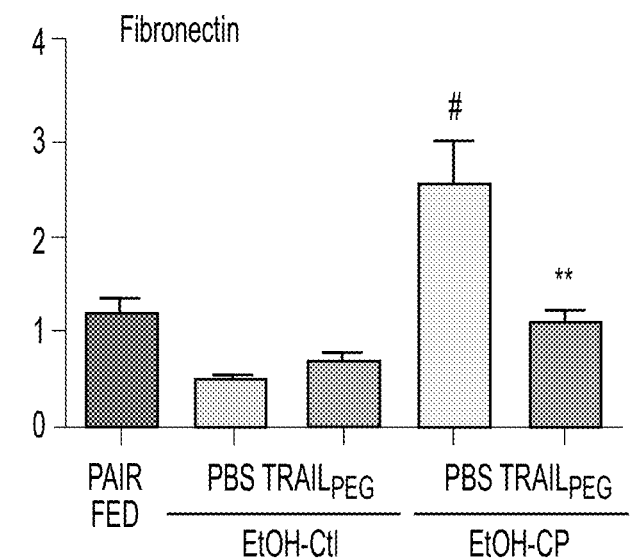
Figure 14G:
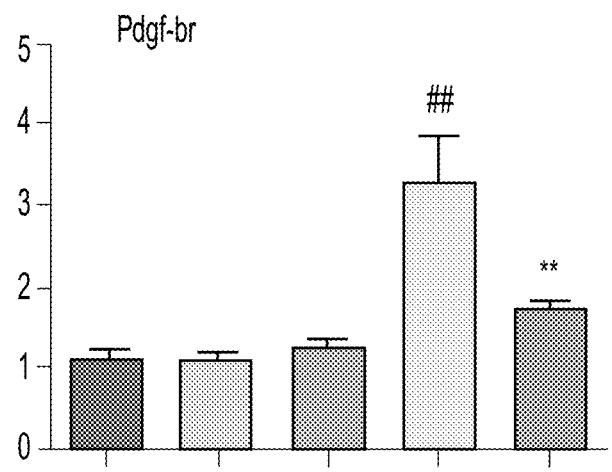
Figure 14H:
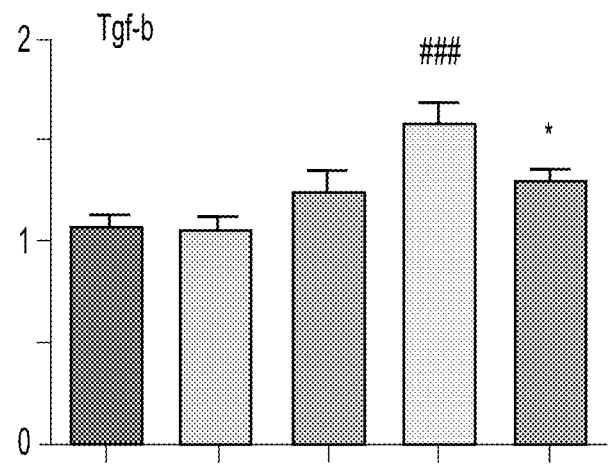
Figure 14I:
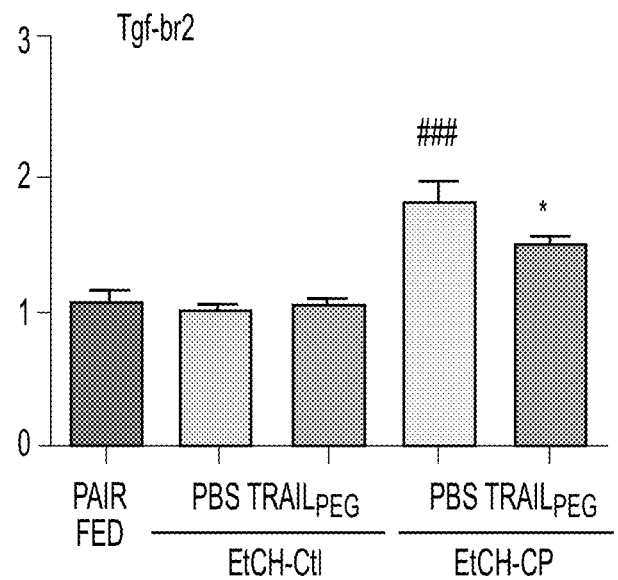

A model of experimental alcohol-induced chronic pancreatitis (CP) was induced in rats (Bertola, A., et al., Nat Protoc, 2013. 8(3):627-637; Deng, X., et al., Am J Pathol, 2005. 166(1):93-106). As shown in FIG. 12, four groups of rats (n=8, each group) were fed a Lieber-Decarli (LD) liquid diet with gradually increased EtOH concentrations from 0 to 36% for seven days and then fed 36% EtOH for up to six weeks. Rats were treated with cerulein (four hourly i.p. injections) on day 14, 21, 28, 35, and 41. $TRAIL_{PEG}$ (4 mg/kg, i.v.) or PBS (control) was injected daily for 7 days beginning on day 36. Two control groups without alcohol in diet were intravenously treated with PBS or $TRAIL_{PEG}$.

Von Frey Filament (VFF) methods are important tools for the study of mechanisms of pain in rodents (Zhu et al., Mol Pain, 8:65(2012)). After treatments on day 43 VFF testing were used to study nociception. After VFF study, animals were sacrificed and pancreas specimens were harvested and analyzed by IHC, qPCR and western blotting. Hydroxyproline (collagen marker) levels in pancreatic tissues were analyzed by hydroxyproline assay kit (Sigma).

Results

Figure 11:
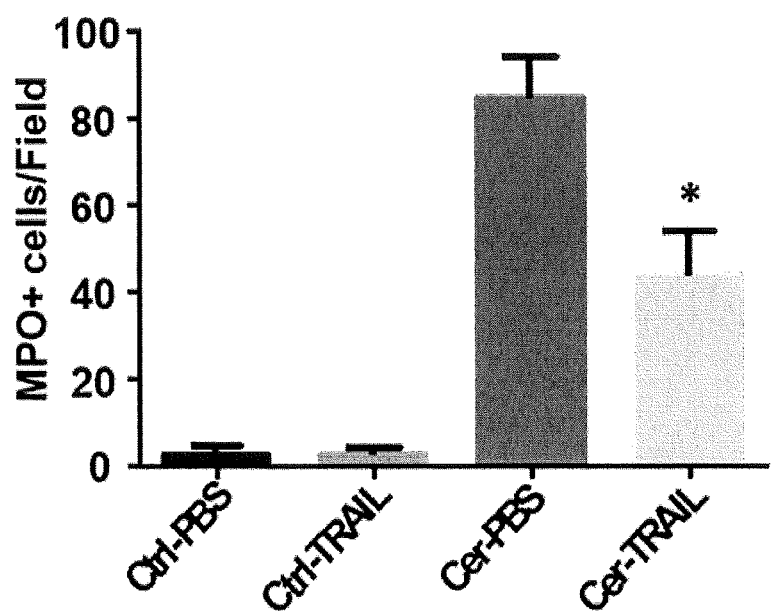
FIG. 11 is a bar graph showing reduced numbers of MPO+ (neutrophil marker) cells in TRAIL$_{PEG}$-treated AP rats. TRAIL$_{PEG}$ treatment significantly reduced inflammation and numbers of infiltrated MPO+ cell infiltrations in the pancreas. *$P<0.05$ vs; Cer-PBS (untreated AP rats).

Photos of pancreatic tissues stained with H&E and immunostained for infiltrating neutrophil (MPO) demonstrated anti-inflammatory efficacy of $TRAIL_{PEG}$ (Cer-TRAIL) when compared to that of PBS-treated AP groups (Cer-PBS). Intravenous $TRAIL_{PEG}$ (Cer-TRAIL) protects acute pancreatitis (AP) in cerulein-induced AP rats (Cer-PBS). Quantified results are shown in FIG. 11.

Figure 15:
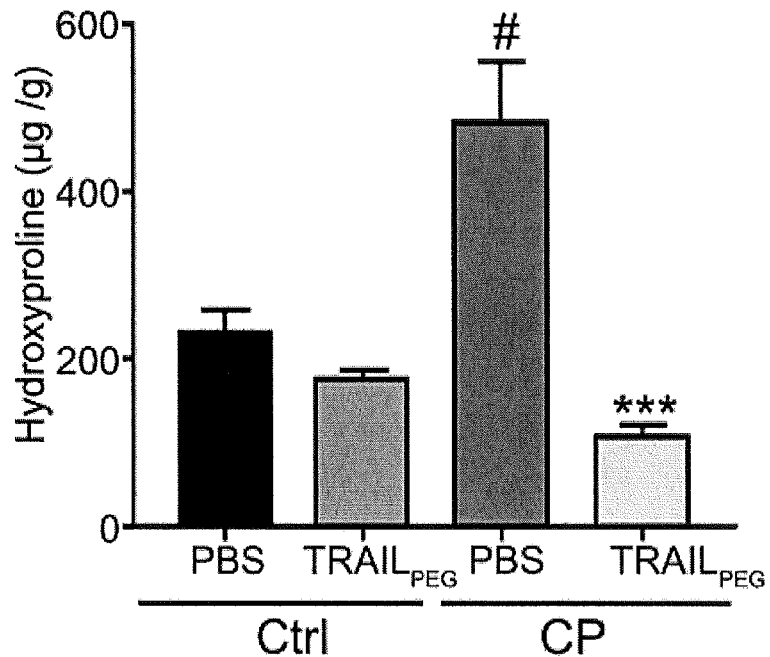
FIG. 15 is a bar graph showing hydroxyproline concentration (µg/g) (collagen marker) in pancreatic tissues of control and CP rats (EtOH-CP) treated with PBS or TRAIL$_{PEG}$. TRAIL$_{PEG}$ significantly reduces hydroxyproline levels in the pancreas in cerulein- and ethanol/Lieber DeCarli diet-induced CP rats (EtOH-CP) compared to non-treated EtOH-CP. #$P<0.05$ vs. Ctrl groups, ***$P<0.001$ vs. EtOH-CP/PBS.

In the CP models, pancreatic fibrogenesis was demonstrated by high expression of collagen and α-SMA (activated PSC marker) (FIGS. 13A and 13B) and multiple fibrogenic markers (FIGS. 14A-14I). $TRAIL_{PEG}$ treatment significantly reduced collagen depositions, down-regulated α-SMA and PDGFRβ as well as other fibrogenic and pancreatitis markers including collagens (Col1a2, Col3a1), TIMPs (tissue inhibitor of metalloproteinases), fibronectin, Pap (pancreatitis associated protein) and TGFβ (FIGS. 14A-14I). Hydroxyproline levels were highly increased in CP models. $TRAIL_{PEG}$ treatment significantly reduced hydroxyproline contents in the pancreas (FIG. 15). Cleaved caspase-8 was significantly upregulated only in $TRAIL_{PEG}$-treated CP, indicating that eradication of activated PSCs may be due to TRAIL-mediated apoptosis. Importantly, through double immunostating of pancreatic tissues (aPSCs—α-SMA staining, apoptosis—TUNEL staining, and nucleus—DAPI staining, one was able to validate that apoptosis (TUNEL staining) was specifically occurred in α-SMA+ aPSCs. Systemic administration of $TRAIL_{PEG}$ alone to normal rats did not induce any noticeable toxicity. For example, $TRAIL_{PEG}$ treatment significantly normalized ALT levels, a useful maker of liver damage, compared to that on non-treated CP rats.

CP is accompanied by severe and constant abdominal pain. Surprisingly, TRAIL$_{PEG}$ showed anti-nociceptive efficacy in the CP models. TRAIL$_{PEG}$ decreased somatic referred hyperalgesia in ethanol/cerulein/LD diet-induced CP rats. TRAIL$_{PEG}$ (4 mg/kg, i.v.)-treated animals (n=4) demonstrated a significant decline in somatic referred hyperalgesia as measured by VFF testing (FIG. 16). It has now been shown that treatment of DRG neurons with NGF (nerve growth factor) or TGFβ induced changes in their excitability and suppressed a specific voltage dependent potassium current (IA), which is a hallmark of nociceptive excitability in CP (Zhu et al., *Mol Pain*, 8:65(2012). TGFβ can itself sensitize nociceptors, induce pancreatic hyperalgesia. In the preliminary studies, it was validated that PSCs upregulate TGFβ during the activation process and conditioned media (CM) obtained from aPSC affects the excitability of DRG neurons. Activated PSCs (aPSCs) upregulate TGFβ (FIG. 3B) and conditioned media (CM) obtained from aPSC affects the excitability of DRG neurons (FIG. 10). Therefore, activated PSC is a predominant cell type that should be responsible for nociceptive sensitization in the pancreas and PSC activation plays crucial roles in nociceptor sensitization. Therefore, this technique represents a new way to ameliorate pain by selectively blocking PSC activation or depleting activated PSCs, one of the dominant cellular sources for TGFβ and NGF (nerve growth factor), by utilizing death receptor agonists.

We claim:

1. A method of treating pain associated with acute pancreatitis or an acute pancreatic pain disorder comprising administering to a subject suffering from acute pancreatitis or acute pancreatic pain disorder a composition comprising an effective amount of a death receptor agonist selected from the group consisting of recombinant human Tumor necrosis factor (TNF)—related apoptosis inducing ligand (TRAIL) protein, TRAIL analogs, PEGylated TRAIL, death receptor 5 (DR5) agonistic antibodies, and combinations thereof, to reduce pain.

2. The method of claim 1, wherein the death receptor agonist is an agonist of death receptor 5 (DR5).

3. The method of claim 1, wherein the death receptor agonist comprises a DR5 agonist selected from the group consisting of Lexatumumab, Tigatuzumab, Conatumumab, Drozitumab, HGSTR2J/KMTRS, and LBY-135.

4. The method of claim 1, wherein the death receptor agonist comprises a multivalent DR agonist selected from the group consisting of TAS266 and scTRAIL-RBDs.

5. The method of claim 1, wherein the antibodies are full length antibodies, functional fragments thereof retaining binding functionality, humanized antibodies, bifunctional or chimeric antibodies, or combinations thereof.

6. The method of claim 1, wherein the agonist is TRAIL or TRAIL modified with a polyalkylene oxide.

7. The method of claim 6 wherein the polyalkylene oxide is linear, branched, a dimer or trimer polyethylene glycol having a molecular weight between 5,000 and 50,000 daltons.

8. The method of claim 1, wherein the composition is administered via injection.

9. The method of claim 1, wherein pancreatic tissues are protected, fibrotic formation is reduced, pancreatic fibrogenesis is reversed, and healthy pancreatic tissues are unharmed.

10. The method of claim 1, wherein the subject has an acute pancreatic pain disorder.

11. The method of claim 10, wherein the acute pancreatic pain disorder is acute pancreatitis-related pain.

12. The method of claim 1, wherein treating pain associated with acute pancreatitis or an acute pancreatic pain disorder comprises reducing pancreatic inflammation.

13. The method of claim 1, wherein the method reduces pancreatic inflammation without toxicity against normal pancreatic cells.

14. The method of claim 1, wherein the method reduces pancreatic inflammation without toxicity against acinar cells of the pancreas.

15. The method of claim 1, wherein the subject does not have pancreatic cancer.

16. The method of claim 1, wherein an effective amount of the composition is administered once daily, twice daily, trice daily, once weekly, twice weekly, biweekly, or once monthly.

17. The method of claim 1, wherein the composition is administered at a dose between about 0.001 mg/kg and 100 mg/kg.

18. The method of claim 1, wherein the composition is administered at a dose between about 0.2 mg/kg and 20 mg/kg.

\* \* \* \* \*

UNITED STATES PATENT AND TRADEMARK OFFICE
CERTIFICATE OF CORRECTION

PATENT NO. : 11,084,879 B2
APPLICATION NO. : 16/092142
DATED : August 10, 2021
INVENTOR(S) : Lee et al.

It is certified that error appears in the above-identified patent and that said Letters Patent is hereby corrected as shown below:

In the Specification

Column 2, Line 37, replace "death receptor agonist Suitable" with --death receptor agonist. Suitable--.
Column 3, Line 15, replace "daltons As" with --daltons as--.
Column 3, Line 29, replace "lexatumuman" with --lexatumumab--.
Column 4, Line 35, replace "suing" with --using--.
Column 4, Lines 35-36, replace "DR5 predominantly expressed on cellular surface" with --DR5 is predominantly expressed on the cellular surface--.
Column 4, Line 56, replace "induce apoptosis" with --induced apoptosis--.
Column 5, Line 22, replace "a-SMA" with --α-SMA--.
Column 5, Line 32, replace "a-SMA" with --α-SMA--.
Column 5, Line 48, replace "response" with --responses--.
Column 6, Lines 17-19, replace "classifying a pathology or a symptom, determining a severity of the pathology" with --classifying a pathology or a symptom, determining severity of the pathology--.
Column 6, Line 20, replace "outcome of pathology" with --outcome of the pathology--.
Column 6, Line 30, replace "amount of for therapeutic treatment" with --amount for therapeutic treatment--.
Column 7, Line 23, replace "lexatumuman" with --lexatumumab--.
Column 9, Line 32, replace "lexatumuman" with --lexatumumab--.
Column 12, Line 39, replace "a liquid chromatography" with --liquid chromatography--.
Column 12, Line 40, replace "a polarimetry" with --polarimetry--.
Column 12, Line 49, replace "excipient" with --excipients--.
Column 13, Line 22, replace "a site specific site" with --a specific site--.
Column 13, Line 29, replace "etc. made" with --etc. are made--.
Column 14, Line 46, replace "preferably dose" with --a preferable dose--.
Column 14, Line 47, replace "exampled" with --example--.
Column 18, Lines 24-25, replace "pancreas as distinct from reversible changes in" with --pancreas which is distinct from the reversible changes observed in--.

Signed and Sealed this
Eighth Day of February, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,084,879 B2

Column 18, Line 27, replace "50 per 100,000" with --50 per 100,000 people--.
Column 21, Lines 41-42, replace "administering to a a mammal" with --administering to a mammal--.
Column 21, Line 59, replace "administer" with --administered--.
Column 22, Line 31, replace "after to the first" with --after the first--.
Column 22, Line 35, replace "administering of the second" with --administering the second--.
Column 22, Line 42, replace "administration of second" with --administration of the second--.
Column 22, Line 66, replace "acceptable carrier" with --acceptable carriers--.
Column 24, Lines 19-20, replace "TRIALPEG" with --TRAILPEG--.
Column 24, Line 29, replace "extracellular Matrix" with --extracellular matrix--.
Column 24, Line 44, replace "TRIAL-Induced" with --TRAIL-induced--.
Column 25, Line 42, replace "Casep-8" with --Casp-8--.
Column 26, Line 11, replace "caspase3/7" with --caspase 3/7--.
Column 26, Line 63, replace "a-SMA" with --α-SMA--.
Column 27, Line 10, replace "Col1α2" with --Col1a2--.
Column 27, Line 19, replace "contumumab" with --conatumumab--.
Column 27, Line 20, replace "maptumumab" with --mapatumumab--.
Column 27, Line 22, replace "contumumab" with --conatumumab--.
Column 27, Lines 23-24, replace "maptumumab" with --mapatumumab--.
Column 28, Lines 59-60, replace "a-SMA" with --α-SMA--.
Column 28, Line 62, replace "was specifically occurred" with --specifically occurred--.
Column 28, Line 66, replace "maker" with --marker--.
Column 28, Line 66, replace "that on non-" with --that of non- --.

SEQUENCE LISTING

<160> NUMBER OF SEQ ID NOS: 2

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

```
Ser Phe Phe Gly Ala Phe Leu Val Gly
        275                 280

<210> SEQ ID NO 2
<211> LENGTH: 167
<212> TYPE: PRT
<213> ORGANISM: Homo sapiens

<400> SEQUENCE: 2

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
                100                 105                 110

Arg Asn Ser Cys Trp Ser Lys Asp Ala Glu Tyr Gly Leu Tyr Ser Ile
            115                 120                 125

Tyr Gln Gly Gly Ile Phe Glu Leu Lys Glu Asn Asp Arg Ile Phe Val
        130                 135                 140

Ser Val Thr Asn Glu His Leu Ile Asp Met Asp His Glu Ala Ser Phe
145                 150                 155                 160

Phe Gly Ala Phe Leu Val Gly
                165
```